United States Patent
Worden et al.

(10) Patent No.: US 10,598,650 B2
(45) Date of Patent: Mar. 24, 2020

(54) SYSTEM AND METHOD FOR MEASURING AN OPERATIVE CONDITION OF A MACHINE

(71) Applicant: General Electric Company, Schenectady, NY (US)

(72) Inventors: Bret Dwayne Worden, Lawrence Park, PA (US); Mahalakshmi Shunmugham Balasubramaniam, Bangalore (IN); Ajith Kuttannair Kumar, Lawrence Park, PA (US); Jingjun Zhang, Lawrence Park, PA (US); Jennifer Lynn Coyne, Lawrence Park, PA (US); Sachidananda Chinagudi Jagadeesha, Bangalore (IN)

(73) Assignee: General Electric Company, Schenectady, NY (US)

( * ) Notice: Subject to any disclaimer, the term of this patent is extended or adjusted under 35 U.S.C. 154(b) by 312 days.

(21) Appl. No.: 14/869,038

(22) Filed: Sep. 29, 2015

(65) Prior Publication Data
US 2016/0018382 A1    Jan. 21, 2016

Related U.S. Application Data

(63) Continuation-in-part of application No. 14/421,245, filed as application No. PCT/US2013/055983 on Aug. 21, 2013, now Pat. No. 9,746,452.

(60) Provisional application No. 61/692,230, filed on Aug. 22, 2012.

(51) Int. Cl.
    *G01N 33/28*      (2006.01)

(52) U.S. Cl.
    CPC .............................. *G01N 33/2888* (2013.01)

(58) Field of Classification Search
    CPC ................................................. G01N 33/2888
    See application file for complete search history.

(56) References Cited

U.S. PATENT DOCUMENTS

| | | |
|---|---|---|
| D218,009 S | 7/1970 | Bosack |
| D219,617 S | 12/1970 | Swift |

(Continued)

FOREIGN PATENT DOCUMENTS

| | | |
|---|---|---|
| AU | 2015268746 A1 | 7/2016 |
| CN | 1363844 A | 8/2002 |

(Continued)

OTHER PUBLICATIONS

Rakow et al., "A Colorimetric Sensor Array for Odour Visualization", Nature, vol. No. 406, pp. 710-713, Aug. 17, 2000.

(Continued)

*Primary Examiner* — Herbert K Roberts
(74) *Attorney, Agent, or Firm* — Armstrong Teasdale LLP

(57) ABSTRACT

A system includes a sensor, one or more processors, a transmitter, and a capacitance control structure. The sensor is configured to contact a fluid and measure a characteristic of the fluid. The one or more processors are operably coupled to the sensor. The one or more processors are configured to generate one or more data signals representative of the characteristic of the fluid that is measured by the sensor. The transmitter is operably coupled to the one or more processors. The transmitter is configured to wirelessly communicate the one or more data signals to a remote reader. The capacitance control structure is configured to one or more of reduce or isolate sensor capacitance of the sensor from the one or more processors.

20 Claims, 11 Drawing Sheets

(56) References Cited

U.S. PATENT DOCUMENTS

| | | |
|---|---|---|
| 3,675,121 A | 7/1972 | Thompson |
| 3,778,706 A | 12/1973 | Thompson |
| 3,927,369 A | 12/1975 | Billeter et al. |
| 4,096,385 A | 6/1978 | Marett |
| 4,219,805 A | 8/1980 | Magee et al. |
| 4,273,636 A | 6/1981 | Shimada et al. |
| 4,275,364 A | 6/1981 | Skatvold, Jr. |
| 4,349,882 A | 9/1982 | Asmundsson et al. |
| 4,372,164 A | 2/1983 | Brown et al. |
| 4,553,434 A | 11/1985 | Spaargaren |
| 4,728,892 A | 3/1988 | Vinegar et al. |
| 4,745,893 A | 5/1988 | Atherton et al. |
| 4,806,847 A | 2/1989 | Atherton et al. |
| 4,820,989 A | 4/1989 | Vail, III |
| 4,844,097 A | 7/1989 | Bellhouse et al. |
| 4,876,512 A | 10/1989 | Kroeger et al. |
| 4,882,542 A | 11/1989 | Vail, III |
| 4,887,455 A | 12/1989 | Payne et al. |
| 4,887,798 A | 12/1989 | Julius |
| 4,922,745 A | 5/1990 | Rudkin et al. |
| 4,941,958 A | 7/1990 | Byers |
| 4,965,522 A | 10/1990 | Hazen et al. |
| 4,996,490 A | 2/1991 | Scott et al. |
| 5,010,301 A | 4/1991 | Leung et al. |
| 5,025,346 A | 6/1991 | Tang et al. |
| 5,059,790 A | 10/1991 | Klainer et al. |
| 5,089,780 A | 2/1992 | Megerle |
| 5,138,880 A | 8/1992 | Lee et al. |
| 5,157,338 A | 10/1992 | Motherbaugh et al. |
| 5,208,165 A | 5/1993 | Law et al. |
| 5,241,364 A | 8/1993 | Kimura |
| 5,260,569 A | 11/1993 | Kimura |
| 5,306,644 A | 4/1994 | Myerholtz et al. |
| 5,344,547 A | 9/1994 | Vlasov et al. |
| 5,421,983 A | 6/1995 | Slack et al. |
| 5,443,985 A | 8/1995 | Lu et al. |
| 5,497,140 A | 3/1996 | Tuttle |
| 5,543,722 A | 8/1996 | Suzuki et al. |
| 5,591,896 A | 1/1997 | Lin |
| 5,592,040 A | 1/1997 | Yamamoto |
| 5,607,566 A | 3/1997 | Brown et al. |
| 5,646,592 A | 7/1997 | Tuttle |
| 5,672,319 A | 9/1997 | Eisum |
| 5,744,902 A | 4/1998 | Vig |
| 5,751,475 A | 5/1998 | Ishiwata et al. |
| 5,754,055 A | 5/1998 | McAdoo et al. |
| 5,785,181 A | 7/1998 | Quartararo, Jr. |
| 5,786,595 A | 7/1998 | Herron et al. |
| 5,817,943 A | 10/1998 | Welles, II et al. |
| 5,831,439 A | 11/1998 | Suenram et al. |
| 5,840,168 A | 11/1998 | Chaniotakis et al. |
| 5,874,047 A | 2/1999 | Schoning et al. |
| 5,961,923 A | 10/1999 | Nova et al. |
| 6,025,725 A | 2/2000 | Gershenfeld et al. |
| 6,025,783 A | 2/2000 | Steffens, Jr. |
| 6,111,520 A | 8/2000 | Allen et al. |
| 6,166,546 A | 12/2000 | Scheihing et al. |
| 6,189,656 B1 | 2/2001 | Morgenstern et al. |
| 6,192,753 B1 | 2/2001 | Czarnek |
| 6,204,764 B1 | 3/2001 | Maloney |
| 6,250,152 B1 * | 6/2001 | Klein .................. G01F 23/268 |
| | | 324/690 |
| 6,278,379 B1 | 8/2001 | Allen et al. |
| 6,287,765 B1 | 9/2001 | Cubicciotti |
| 6,359,444 B1 | 3/2002 | Grimes |
| 6,360,585 B1 | 3/2002 | Potyrailo et al. |
| 6,380,750 B1 | 4/2002 | Schenck et al. |
| 6,398,931 B1 | 6/2002 | Burchette et al. |
| 6,399,375 B2 | 6/2002 | Vajta |
| 6,406,668 B1 | 6/2002 | Dordick et al. |
| 6,461,872 B1 | 10/2002 | Sivavec et al. |
| 6,470,735 B1 * | 10/2002 | Bell .................. F01M 11/10 |
| | | 184/6.4 |
| 6,471,838 B1 | 10/2002 | Igel et al. |
| 6,506,346 B1 | 1/2003 | Monro |
| 6,544,193 B2 | 4/2003 | Abreu |
| 6,586,946 B2 | 7/2003 | Hefti et al. |
| 6,614,229 B1 | 9/2003 | Clark et al. |
| 6,657,429 B1 | 12/2003 | Goldfine et al. |
| 6,672,512 B2 | 1/2004 | Bridgelall |
| 6,676,903 B2 | 1/2004 | Potyrailo et al. |
| 6,730,201 B1 | 5/2004 | Kuhlman et al. |
| 6,751,557 B1 | 6/2004 | Shehab et al. |
| 6,771,074 B2 | 8/2004 | Zou et al. |
| 6,773,926 B1 | 8/2004 | Freund et al. |
| 6,780,307 B2 | 8/2004 | Kidwell |
| 6,782,736 B1 | 8/2004 | Hammer |
| 6,804,544 B2 | 10/2004 | Van Antwerp et al. |
| 6,818,450 B2 | 11/2004 | Eaton et al. |
| 6,864,801 B2 | 3/2005 | Tabanou et al. |
| 6,891,383 B2 | 5/2005 | Nicholson et al. |
| 6,911,818 B2 | 6/2005 | Julius |
| 6,953,520 B2 | 10/2005 | Yengoyan et al. |
| 7,017,404 B1 | 3/2006 | Kain |
| 7,031,560 B2 | 4/2006 | Lelong-Feneyrou et al. |
| 7,034,660 B2 | 4/2006 | Watters et al. |
| 7,038,470 B1 | 5/2006 | Johnson |
| 7,076,858 B2 | 7/2006 | Eckstein et al. |
| 7,113,125 B2 | 9/2006 | Le Sesne |
| 7,126,013 B2 | 10/2006 | Heeney et al. |
| 7,168,310 B2 | 1/2007 | Al-Ruwaili |
| 7,171,312 B2 | 1/2007 | Steinthal et al. |
| 7,178,416 B2 | 2/2007 | Whelan et al. |
| 7,204,128 B1 | 4/2007 | Liu et al. |
| 7,252,010 B2 | 8/2007 | Ohta et al. |
| 7,276,916 B2 | 10/2007 | Hammer |
| 7,293,450 B2 | 11/2007 | Liu et al. |
| 7,317,989 B2 | 1/2008 | Difoggio et al. |
| 7,335,336 B1 | 2/2008 | Kim |
| 7,350,367 B2 | 4/2008 | Matsiev et al. |
| 7,434,457 B2 | 10/2008 | Goodwin et al. |
| 7,445,143 B2 | 11/2008 | Pang et al. |
| 7,449,893 B1 | 11/2008 | Tsironis |
| 7,455,108 B2 | 11/2008 | Jenkins et al. |
| 7,456,744 B2 | 11/2008 | Kuhns |
| 7,466,041 B2 | 12/2008 | Urman |
| 7,481,771 B2 | 1/2009 | Fonseca et al. |
| 7,483,743 B2 | 1/2009 | Mann et al. |
| 7,486,495 B1 | 2/2009 | Diederichs et al. |
| 7,495,454 B2 | 2/2009 | Rivera |
| 7,523,647 B2 | 4/2009 | Scott |
| 7,562,557 B2 | 7/2009 | Bennett et al. |
| 7,569,810 B1 | 8/2009 | Troxler et al. |
| 7,629,167 B2 | 12/2009 | Hodge et al. |
| 7,677,307 B2 | 3/2010 | Vasques et al. |
| 7,688,218 B2 | 3/2010 | Lefebvre et al. |
| 7,808,235 B2 | 10/2010 | Rollins et al. |
| 7,812,609 B2 | 10/2010 | Martinez et al. |
| 7,911,345 B2 | 3/2011 | Potyrailo et al. |
| 7,948,380 B2 | 5/2011 | Kuhns et al. |
| 7,948,385 B2 | 5/2011 | Potyrailo et al. |
| 7,958,772 B2 | 6/2011 | Permuy et al. |
| 7,969,307 B2 | 6/2011 | Peeters |
| 8,018,342 B2 | 9/2011 | Monk et al. |
| 8,111,143 B2 | 2/2012 | Tong et al. |
| 8,155,891 B2 | 4/2012 | Kong et al. |
| 8,159,347 B2 | 4/2012 | Potyrailo et al. |
| 8,184,290 B2 | 5/2012 | Hertens et al. |
| 8,190,394 B2 | 5/2012 | Davis et al. |
| 8,232,091 B2 | 7/2012 | Maltezos et al. |
| 8,246,910 B2 | 8/2012 | Dhirani et al. |
| 8,261,618 B2 | 9/2012 | Engle et al. |
| 8,318,099 B2 | 11/2012 | Potyrailo et al. |
| 8,342,242 B2 | 1/2013 | Roddy et al. |
| 8,429,985 B2 | 4/2013 | Furlong |
| 8,452,716 B2 | 5/2013 | Howley et al. |
| 8,508,368 B2 | 8/2013 | Potyrailo et al. |
| 8,542,023 B2 | 9/2013 | Potyrailo et al. |
| 8,542,024 B2 | 9/2013 | Potyrailo et al. |
| 8,547,110 B2 | 10/2013 | Kesil et al. |
| 8,643,388 B2 | 2/2014 | Hedges |
| 8,676,436 B2 | 3/2014 | Raimarckers et al. |
| 8,710,973 B2 | 4/2014 | Schneider et al. |
| 8,732,938 B2 | 5/2014 | Kolosov et al. |

(56) References Cited

U.S. PATENT DOCUMENTS

| | | | |
|---|---|---|---|
| 8,736,425 B2 | 5/2014 | Potyrailo | |
| 8,833,145 B2 | 9/2014 | Fischer et al. | |
| 8,933,706 B1 | 1/2015 | Karlquist | |
| 8,952,708 B2 | 2/2015 | Nikolenko | |
| 9,045,973 B2 | 6/2015 | Potyrailo et al. | |
| 9,074,966 B2 | 7/2015 | Sanderlin et al. | |
| 9,097,639 B2 | 8/2015 | Potyrailo et al. | |
| 9,195,925 B2 | 11/2015 | Potyrailo et al. | |
| 9,261,474 B2 | 2/2016 | Potyrailo et al. | |
| 9,389,260 B2 | 7/2016 | Potyrailo et al. | |
| 9,536,122 B2 | 1/2017 | Potyrailo | |
| 9,538,657 B2 | 1/2017 | Potyrailo et al. | |
| D778,189 S | 2/2017 | Worden et al. | |
| 9,589,686 B2 | 3/2017 | Potyrailo et al. | |
| 2001/0045355 A1 | 11/2001 | Gephart et al. | |
| 2002/0008526 A1 | 1/2002 | Martin et al. | |
| 2002/0050929 A1 | 5/2002 | Parrotta et al. | |
| 2002/0081231 A1 | 6/2002 | Shapiro et al. | |
| 2002/0089356 A1 | 7/2002 | Perrott et al. | |
| 2002/0149466 A1 | 10/2002 | Sunshine et al. | |
| 2002/0173040 A1 | 11/2002 | Potyrailo et al. | |
| 2002/0174712 A1* | 11/2002 | Hubrich | F01M 11/10 73/54.01 |
| 2002/0177232 A1 | 11/2002 | Melker et al. | |
| 2003/0053936 A1 | 3/2003 | Potyrailo et al. | |
| 2003/0154031 A1 | 8/2003 | Potyrailo et al. | |
| 2003/0179024 A1 | 9/2003 | Montagnana | |
| 2003/0232223 A1 | 12/2003 | Leddy et al. | |
| 2004/0015990 A1 | 1/2004 | Suematsu et al. | |
| 2004/0035211 A1 | 2/2004 | Pinto et al. | |
| 2004/0051154 A1 | 3/2004 | Yamakawa et al. | |
| 2004/0113790 A1 | 6/2004 | Hamel et al. | |
| 2004/0125442 A1 | 7/2004 | Yun et al. | |
| 2004/0155667 A1 | 8/2004 | Kesil et al. | |
| 2004/0189487 A1 | 9/2004 | Hoefel et al. | |
| 2004/0219523 A1 | 11/2004 | Stanton et al. | |
| 2004/0227682 A1 | 11/2004 | Anderson | |
| 2004/0248315 A1 | 12/2004 | Klein et al. | |
| 2005/0022581 A1 | 2/2005 | Sunshine | |
| 2005/0058460 A1 | 3/2005 | Wang | |
| 2005/0093760 A1 | 5/2005 | Rochelle et al. | |
| 2005/0161405 A1 | 7/2005 | Holland | |
| 2005/0193832 A1 | 9/2005 | Tombs et al. | |
| 2005/0199731 A9 | 9/2005 | Empedocles et al. | |
| 2005/0261562 A1 | 11/2005 | Zhou et al. | |
| 2006/0014172 A1 | 1/2006 | Muller et al. | |
| 2006/0020427 A1 | 1/2006 | Kahn et al. | |
| 2006/0055531 A1 | 3/2006 | Cook et al. | |
| 2006/0081471 A1 | 4/2006 | Kidwell | |
| 2006/0133720 A1 | 6/2006 | Hochberg et al. | |
| 2006/0141469 A1 | 6/2006 | Rossier et al. | |
| 2006/0198760 A1 | 9/2006 | Potyrailo et al. | |
| 2006/0205093 A1 | 9/2006 | Prins | |
| 2006/0210440 A1 | 9/2006 | Potyrailo et al. | |
| 2006/0238349 A1 | 10/2006 | Hu et al. | |
| 2006/0265150 A1 | 11/2006 | Hu et al. | |
| 2007/0029195 A1 | 2/2007 | Li et al. | |
| 2007/0064839 A1 | 3/2007 | Luu | |
| 2007/0084277 A1 | 4/2007 | Steinsiek | |
| 2007/0085686 A1 | 4/2007 | Oz | |
| 2007/0090926 A1 | 4/2007 | Potyrailo et al. | |
| 2007/0111222 A1 | 5/2007 | Chasin et al. | |
| 2007/0131418 A1 | 6/2007 | Barrow et al. | |
| 2007/0148670 A1 | 6/2007 | O'Malley | |
| 2007/0176773 A1 | 8/2007 | Smolander et al. | |
| 2007/0236338 A1 | 10/2007 | Maruyama | |
| 2007/0241890 A1 | 10/2007 | Yoshioka | |
| 2008/0012577 A1 | 1/2008 | Potyrailo et al. | |
| 2008/0093219 A1 | 4/2008 | Goldberg et al. | |
| 2008/0116908 A1 | 5/2008 | Potyrailo et al. | |
| 2008/0135614 A1 | 6/2008 | Werner et al. | |
| 2008/0142366 A1 | 6/2008 | Tamirisa et al. | |
| 2008/0157901 A1 | 7/2008 | Matekovits et al. | |
| 2008/0177150 A1 | 7/2008 | Il et al. | |
| 2008/0179197 A1 | 7/2008 | Wu | |
| 2008/0180249 A1 | 7/2008 | Butler et al. | |
| 2008/0184787 A1 | 8/2008 | Coates | |
| 2008/0191859 A1 | 8/2008 | Tiek et al. | |
| 2008/0236814 A1 | 10/2008 | Roddy | |
| 2008/0280374 A1 | 11/2008 | Potyrailo et al. | |
| 2008/0300746 A1* | 12/2008 | Dreier | B60R 16/0234 701/31.4 |
| 2009/0035856 A1 | 2/2009 | Galliher et al. | |
| 2009/0039864 A1 | 2/2009 | Gordon | |
| 2009/0087862 A1 | 4/2009 | Carter et al. | |
| 2009/0095073 A1 | 4/2009 | Fukumura et al. | |
| 2009/0104707 A1 | 4/2009 | Wang et al. | |
| 2009/0120169 A1 | 5/2009 | Chandler et al. | |
| 2009/0189741 A1 | 7/2009 | Rowland et al. | |
| 2009/0204250 A1 | 8/2009 | Potyrailo et al. | |
| 2009/0215646 A1 | 8/2009 | Anslyn et al. | |
| 2009/0235781 A1* | 9/2009 | Quehenberger | B60K 17/02 74/665 F |
| 2009/0256679 A1 | 10/2009 | Potyrailo et al. | |
| 2009/0265037 A1 | 10/2009 | Bassa | |
| 2009/0289776 A1 | 11/2009 | Moore et al. | |
| 2009/0308155 A1 | 12/2009 | Zhang | |
| 2010/0021993 A1 | 1/2010 | Wang et al. | |
| 2010/0042338 A1 | 2/2010 | Giurgiutiu et al. | |
| 2010/0059221 A1 | 3/2010 | Vannuffelen et al. | |
| 2010/0075405 A1 | 3/2010 | Broadley et al. | |
| 2010/0102004 A1 | 4/2010 | Holland | |
| 2010/0109766 A1 | 5/2010 | Nilsson et al. | |
| 2010/0134286 A1 | 6/2010 | Potyrailo et al. | |
| 2010/0138267 A1 | 6/2010 | Vittal et al. | |
| 2010/0153323 A1 | 6/2010 | Hennessy et al. | |
| 2010/0231407 A1 | 9/2010 | Carr | |
| 2010/0250170 A1 | 9/2010 | Kalinin et al. | |
| 2010/0261226 A1 | 10/2010 | Niazi | |
| 2010/0268479 A1 | 10/2010 | Potyrailo et al. | |
| 2010/0280788 A1 | 11/2010 | Bohan et al. | |
| 2010/0295558 A1 | 11/2010 | Eberheim et al. | |
| 2011/0006878 A1 | 1/2011 | Nyffeler et al. | |
| 2011/0006900 A1 | 1/2011 | Nyffeler et al. | |
| 2011/0012736 A1 | 1/2011 | Potyrailo et al. | |
| 2011/0018649 A1 | 1/2011 | David et al. | |
| 2011/0022318 A1 | 1/2011 | Zhao et al. | |
| 2011/0029156 A1 | 2/2011 | Vernacchia et al. | |
| 2011/0045601 A1 | 2/2011 | Gryska et al. | |
| 2011/0051775 A1 | 3/2011 | Ivanov et al. | |
| 2011/0117538 A1 | 5/2011 | Niazi | |
| 2011/0152706 A1 | 6/2011 | Christopherson et al. | |
| 2011/0152750 A1 | 6/2011 | Dacey, Jr. et al. | |
| 2011/0156177 A1 | 6/2011 | Merz | |
| 2011/0160681 A1 | 6/2011 | Dacey, Jr. et al. | |
| 2011/0221667 A1 | 9/2011 | Lee | |
| 2011/0248825 A1 | 10/2011 | Hamel et al. | |
| 2011/0263036 A1 | 10/2011 | Blauw et al. | |
| 2011/0282540 A1 | 11/2011 | Armitage et al. | |
| 2011/0283821 A1 | 11/2011 | Ober et al. | |
| 2011/0320142 A1 | 12/2011 | Surman et al. | |
| 2012/0001730 A1 | 1/2012 | Potyrailo et al. | |
| 2012/0004851 A1 | 1/2012 | Potyrailo et al. | |
| 2012/0025526 A1 | 2/2012 | Luo et al. | |
| 2012/0053881 A1 | 3/2012 | Schulz et al. | |
| 2012/0166095 A1 | 6/2012 | Potyrailo et al. | |
| 2012/0231504 A1 | 9/2012 | Niazi | |
| 2012/0235690 A1 | 9/2012 | Potyrailo et al. | |
| 2012/0258441 A1 | 10/2012 | Gebauer et al. | |
| 2012/0265036 A1 | 10/2012 | Estes et al. | |
| 2012/0289757 A1 | 11/2012 | Boyden et al. | |
| 2012/0290156 A1* | 11/2012 | Woo | B61L 3/006 701/19 |
| 2013/0041334 A1 | 2/2013 | Prioleau et al. | |
| 2013/0060112 A1 | 3/2013 | Pryor et al. | |
| 2013/0181829 A1* | 7/2013 | Schnitz | G06Q 10/08 340/539.1 |
| 2013/0182819 A1 | 7/2013 | Dvorkin et al. | |
| 2013/0285677 A1 | 10/2013 | Hammer | |
| 2013/0304312 A1* | 11/2013 | Dorr | F01M 11/12 701/34.4 |
| 2014/0130587 A1 | 5/2014 | Von Herzen et al. | |
| 2014/0305194 A1 | 10/2014 | Surman et al. | |
| 2015/0115983 A1 | 4/2015 | Potyrailo et al. | |

(56) References Cited

U.S. PATENT DOCUMENTS

| | | |
|---|---|---|
| 2015/0185173 A1 | 7/2015 | Potyrailo et al. |
| 2015/0198578 A1 | 7/2015 | Worden et al. |
| 2015/0233887 A1 | 8/2015 | Surman et al. |
| 2016/0187277 A1 | 6/2016 | Potyrailo et al. |

FOREIGN PATENT DOCUMENTS

| | | |
|---|---|---|
| CN | 1532372 A | 9/2004 |
| CN | 2809215 Y | 8/2006 |
| CN | 1865966 A | 11/2006 |
| CN | 101022760 A | 8/2007 |
| CN | 101057124 A | 10/2007 |
| CN | 201000455 Y | 1/2008 |
| CN | 101988574 A | 3/2011 |
| CN | 102022264 A | 4/2011 |
| CN | 102422330 A | 4/2012 |
| CN | 103575479 A | 2/2014 |
| CN | 203923208 U | 11/2014 |
| CN | 104583664 A | 4/2015 |
| EP | 1173613 A2 | 1/2002 |
| EP | 2498076 A1 | 9/2012 |
| GB | 793953 A | 4/1958 |
| JP | 5774097 A | 5/1982 |
| JP | 59116855 U | 8/1984 |
| JP | 59160746 A | 9/1984 |
| JP | 0381659 A | 4/1991 |
| JP | 06160317 A | 6/1994 |
| JP | 06194333 A | 7/1994 |
| JP | 6086057 U | 12/1994 |
| JP | 0773282 A | 3/1995 |
| JP | 07120423 A | 5/1995 |
| JP | 08509549 A | 10/1996 |
| JP | 09292453 A | 11/1997 |
| JP | 10504388 A | 4/1998 |
| JP | 2000111547 A | 4/2000 |
| JP | 2001502791 A | 2/2001 |
| JP | 2002125206 A | 4/2002 |
| JP | 2003503011 A | 1/2003 |
| JP | 2003506706 A | 2/2003 |
| JP | 2003161637 A | 6/2003 |
| JP | 2005156569 A | 6/2005 |
| JP | 2006516721 A | 7/2006 |
| JP | 2007516509 A | 6/2007 |
| JP | 2008129009 A | 6/2008 |
| JP | 2008236617 A | 10/2008 |
| JP | 2008298565 A | 12/2008 |
| JP | 2009092633 A | 4/2009 |
| JP | 2009538433 A | 11/2009 |
| JP | 2009540292 A | 11/2009 |
| JP | 2011258627 A | 12/2011 |
| WO | 9845779 A1 | 10/1998 |
| WO | 0055583 A1 | 9/2000 |
| WO | 0173380 A1 | 10/2001 |
| WO | 0212129 A1 | 2/2002 |
| WO | 0223176 A1 | 3/2002 |
| WO | 03050529 A1 | 6/2003 |
| WO | 2004032191 A2 | 4/2004 |
| WO | 2007075619 A1 | 7/2007 |
| WO | 2007101992 A1 | 9/2007 |
| WO | 2008082654 A2 | 7/2008 |
| WO | 2013057630 A1 | 4/2013 |
| WO | 2014/031749 A1 | 2/2014 |
| WO | 2015090358 A1 | 6/2015 |
| WO | 2015128050 A1 | 9/2015 |

OTHER PUBLICATIONS

Taton et al., "Scanometric DNA Array Detection with Nanoparticle Probes", Science, vol. No. 289, Issue No. 5485, pp. 1757-1760, Sep. 8, 2000.

Kaya, "Electrical Spectroscopy of Kaolin and Bentonite Slurries", Turkish Journal of Engineering and Environmental Sciences, vol. No. 25, pp. 345-354, 2001.

Lee, "Increase Oil Production and Reduce Chemical Usage through Separator Level Measurement by Density Profiling", ISA TECH/EXPO Technology Update Conference Proceedings, vol. No. 416, pp. 321-328, 2001.

Foster et al., "Detection of Trace Levels of Water in Oil by Photoacoustic Spectroscopy", Sensors and Actuators B: Chemical, vol. No. 77, Issue No. 3, pp. 620-624, Jul. 10, 2001.

MacDiarmid, ""Synthetic Metals": A Novel Role for Organic Polymers (Nobel Lecturer)", Angewandte Chemie International Edition, vol. No. 40, Issue No. 14, pp. 2581-2590, Jul. 16, 2001.

Shirakawa, "The Discovery of Polyacetylene Film: The Dawning of an Era of Conducting Polymers", Angewandte Chemie International Edition, vol. No. 40, Issue No. 14, pp. 2575-2580, Jul. 16, 2001.

Ong et al., "Design and Application of a Wireless, Passive, Resonant-Circuit Environmental Monitoring Sensor", Sensors and Actuators A: Physical, vol. No. 93, Issue No. 1, pp. 33-43, Aug. 25, 2001.

Mourzina et al., "Development of Multisensor Systems based on Chalcogenide Thin Film Chemical Sensors for the Simultaneous Multicomponent Analysis of Metal Ions in Complex Solutions", Electrochimica Acta, vol. No. 47, Issue No. 1-2, pp. 251-258, Sep. 1, 2001.

Gawad et al., "Micromachined Impedance Spectroscopy Flow Cytometer for Cell Analysis and Particle Sizing", Lab on a Chip, vol. No. 1, Issue No. 1, pp. 76-82, Sep. 2001.

Heeger, "Semiconducting and Metallic Polymers: The Fourth Generation of Polymeric Materials", The Journal of Physical Chemistry B, vol. No. 105, Issue No. 36, pp. 8475-8491, Sep. 13, 2001.

Foster-Mills et al., "Photoacoustic Spectroscopy Detects Water in Oil", Sensors Online, pp. 1-5, Oct. 2001, Retrieved from http://archives.sensorsmag.com/articles/1001/12/pf_main.shtml on Apr. 11, 2016.

Janata, "Electrochemical Sensors and their Impedances: A Tutorial", Critical Reviews in Analytical Chemistry, vol. No. 32, Issue No. 2, pp. 109-120, 2002.

Harpster et al., "A Passive Humidity Monitoring System for In Situ Remote Wireless Testing of Micropackages", Microelectromechanical Systems, vol. No. 11, Issue No. 1, pp. 61-67, Feb. 2002.

Akyildiz et al., "Wireless Sensor Networks: A Survey", Computer Networks, vol. No. 38, Issue No. 4, pp. 393-422, Mar. 15, 2002.

Grimes et al., "Wireless Magnetoelastic Resonance Sensors: A Critical Review", vol. No. 2, Issue No. 7, pp. 294-313, Jul. 23, 2002.

Haes et al., "A Nanoscale Optical Biosensor: Sensitivity and Selectivity of an Approach Based on the Localized Surface Plasmon Resonance Spectroscopy of Triangular Silver Nanoparticles", Journal of the American Chemical Society, vol. No. 124, Issue No. 35, pp. 10596-10604, Aug. 8, 2002.

Ceresa et al., "Rational Design of Potentiometric Trace Level Ion Sensors. A Ag+-Selective Electrode with a 100 ppt Detection Limit", Analytical Chemistry, vol. No. 74, Issue No. 16, pp. 4027-4036, Aug. 15, 2002.

Alary et al.,"Subsea Water Separation: A Cost-Effective Solution for Ultra Deep Water Production", 17th World Petroleum Congress, Rio De Janeiro, Brazil, pp. 47-54, Sep. 1-5, 2002.

Smiechowski et al., "Electrochemical Monitoring of Water-Surfactant Interactions in Industrial Lubricants", Journal of Electroanalytical Chemistry, vol. No. 534, Issue No. 2, pp. 171-180, Oct. 18, 2002.

Butler et al., "Wireless, Passive, Resonant-Circuit, Inductively Coupled, Inductive Strain Sensor", Sensors and Actuators A: Physical, vol. No. 102, Issue No. 1, pp. 61-66, Dec. 1, 2002.

Janata et al., "Conducting Polymers in Electronic Chemical Sensors", Nature Materials, vol. No. 2, pp. 19-24, Jan. 2003.

Johns et al., "Sensitive Indirect Photometric Detection of Inorganic and Small Organic Anions by Capillary Electrophoresis Using Orange G as a Probe Ion", Electrophoresis, vol. No. 24, Issue No. 3, pp. 557-566, Jan. 2003.

Potyrailo et al., "Fluorescence Spectroscopy and Multivariate Spectral Descriptor Analysis for High-Throughput Multiparameter Optimization of Polymerization Conditions of Combinatorial 96-Microreactor Arrays", Journal of Combinatorial Chemistry, vol. No. 5, Issue No. 1, pp. 8-17, Jan.-Feb. 2003.

(56) References Cited

OTHER PUBLICATIONS

Fauveau et al., "Guided-Wave Radar Helps Level-Detection in Harsh Settings", Control Engineering, vol. No. 50, Issue No. 3, pp. 16, Mar. 1, 2003.
Grate et al., "Sorptive Behavior of Monolayer-Protected Gold Nanoparticle Films: Implications for Chemical Vapor Sensing", Analytical Chemistry, vol. No. 75, Issue No. 8, pp. 1868-1879, Apr. 15, 2003.
De Borba et al., "Determination of Sodium at Low NG/L Concentrations in Simulated Power Plant Waters by Ion Chromatography", Journal of Chromatography A, vol. No. 995, Issue No. 1-2, pp. 143-152, May 2, 2003.
Sakharov et al., "Liquid Level Sensor Using Ultrasonic Lamb Waves", Ultrasonics, vol. No. 41, Issue No. 4, pp. 319-322, Jun. 2003.
Kumar et al., "Investigation into the Interaction between Surface-Bound Alkylamines and Gold Nanoparticles", Langmuir, vol. No. 19, Issue No. 15, pp. 6277-6282, Jun. 25, 2003.
Mabic et al., "Adjusting the Quality of Treated Water to Experimental Detection Limits", GIT Labor—Journal, vol. No. 47, pp_ 724-727, Jul. 2003.
Finkenzeller, "RFID Handbook: Fundamentals and Applications in Contactless Smart Cards and Identification", John Wiley & Sons, Ltd, Second Edition, pp. 1-427, Jul. 21, 2003.
Pasquale, "Mechanical Sensors and Actuators", Sensors and Actuators, A: Physical, vol. No. 106, Issue No. 1-3, pp. 142-148, Sep. 15, 2003.
Chopra et al., "Selective Gas Detection Using a Carbon Nanotube Sensor", Applied Physics Letters, vol. No. 83, Issue No. 11, pp. 2280-2282, Sep. 15, 2003.
Bauer et al., "Resonant Nanocluster Technology—From Optical Coding and High Quality Security Features to Biochips", Nanotechnology, vol. No. 14, Issue No. 12, pp. 1289-1311, Nov. 4, 2003.
Wang et al., "A New Technique for Detecting Antifreeze in Engine Oil During Early Stage of Leakage", Sensors and Actuators B: Chemical, vol. No. 96, Issue No. 1-2, pp. 157-164, Nov. 15, 2003.
Briglin et al., "Detection of Organic Mercaptan Vapors using Thin Films of Alkylamine-Passivated Gold Nanocrystals", Langmuir, vol. No. 20, Issue No. 2, pp. 299-305, Jan. 20, 2004.
Shamsipur et al., "New Macrocyclic Diamides as Neutral Ionophores for Highly Selective and Sensitive PVC-Membrane Electrodes for Be2+ Ion", Electroanalysis, vol. No. 16, Issue No. 4, pp. 282-288, Mar. 2004.
Joseph et al., "Chemiresistor Coatings from Pt- and Au-Nanoparticle/Nonanedithiol Films: Sensitivity to Gases and Solvent Vapors", Sensors and Actuators B: Chemical, vol. No. 98, Issue No. 2-3, pp. 188-195, Mar. 15 2004.
Seyfried et al., "Measurement of Soil Water Content with a 50-MHz Soil Dielectric Sensor", Soil Science Society of America, vol. No. 68, Issue No. 2, pp. 394-403, Mar.-Apr. 2004.
Fransen, "New Control System Detects Desalter Problems before Upsets Occur", Agar Corporation, Prepared for Presentation at the AICHE 2004 Spring National Meeting, pp. 1-7, Apr. 2004.
Want et al., "Enabling Ubiquitous Sensing with RFID", Computer, vol. No. 37, Issue No. 4, pp. 84-86, Apr. 2004.
Bennett et al., "Monitoring the Operation of an Oil/Water Separator using Impedance Tomography", Minerals Engineering, vol. No. 17, Issue No. 5, pp. 605-614, May 2004.
Varma et al., "High-Speed Label-Free Detection by Spinning-Disk Micro-Interferometry", Biosensors and Bioelectronics, vol. No. 19, Issue No. 11, pp. 1371-1376, Jun. 15, 2004.
Ikenishi et al., "The Dielectric Characteristics of Agricultural Land for On-site and Real Time Measurement", SICE Annual Conference, Sapporo, Japan, vol. No. 2, pp. 1489-1492, Aug. 4-6, 2004.
Pavlov et al., "Aptamer-Functionalized Au Nanoparticles for the Amplified Optical Detection of Thrombin", Journal of the American Chemical Society, vol. No. 126, Issue No. 38, pp. 11768-11769, Sep. 3, 2004.
Thomas et al., "Conjugated Polymer Sensors: Design Principles Towards Enhanced Versatility", pp. 1-6, Dec. 2004.

Barsoukov et al., "Impedance Spectroscopy: Theory, Experiment, and Applications", Second Edition, pp. 205-264, 2005.
Buhrdorf et al., "Multiparameteric Oil Condition Sensor Based on the Tuning Fork Technology for Automotive Applications", Advanced Microsystems for Automotive Applications, pp. 289-298, 2005.
Holstad et al., "Scattered Gamma Radiation Utilized for Level Measurements in Gravitational Separators", IEEE Sensors, vol. No. 5, Issue No. 2, pp. 175-182, Apr. 2005.
Rose et al., "Sensitivity Gains in Chemosensing by Lasing Action in Organic Polymers", Nature, vol. No. 434, pp. 876-879, Apr. 14, 2005.
Rock et al., "Electronic Nose: Current Status and Future Trends", Chemical Reviews, vol. No. 108, Issue No. 2, pp. 705-725, Jan. 19, 2008.
Diamond et al., "Wireless Sensor Networks and Chemo-/Biosensing", Chemical Reviews, vol. No. 108, Issue No. 2, pp. 652-679, Jan. 24, 2008.
Wang et al., "Aptamer Biosensor for Protein Detection Using Gold Nanoparticles", Analytical Biochemistry, vol. No. 373, Issue No. 2, pp. 213-219, Feb. 15, 2008.
Agoston et al., "A Concept of an Infrared Sensor System for Oil Condition Monitoring", Elektrotechnik & Informationstechnik, vol. No. 125, Issue No. 3, pp. 71-75, Mar. 2008.
Wang et al., "Electrochemical Sensors for Clinic Analysis", Sensors, vol. No. 8, Issue No. 4, pp. 2043-2081, Apr. 2008.
Capone et al., "Metal Oxide Gas Sensor Array for the Detection of Diesel Fuel in Engine Oil", Sensors and Actuators B: Chemical, vol. No. 131, Issue No. 1, pp. 125-133, Apr. 14, 2008.
Potyrailo et al., "Position-Independent Chemical Quantitation with Passive 13.56-MHz Radio Frequency Identification (RFID) Sensors", Talanta, vol. No. 75, Issue No. 3, pp. 624-628, May 15, 2008.
Hempel et al., "Lateral Field Excited Quartz Crystal Resonator Sensors for Determination of Acoustic and Electrical Properties of Liquids", IEEE International Frequency Control Symposium, Honolulu, Hawaii, pp. 705-710, May 19-21, 2008.
Palacios et al., "Rational Design of a Minimal Size Sensor Array for Metal Ion Detection", Journal of the American Chemical Society, vol. No. 130, Issue No. 31, pp. 10307-10314, Jul. 11, 2008.
Kauffman et al., "Carbon Nanotube Gas and Vapor Sensors", Angewandte Chemie International Edition, vol. No. 47, pp. 6550-6570, Jul. 18, 2008.
Zheng et al., "Resonance Impedance Sensing of Human Blood Cells", Sensors and Actuators A: Physical, vol. No. 145-146, pp. 29-36, Jul.-Aug. 2008.
Guan et al., "Engine Lubricating Oil Classification by SAE Grade and Source Based on Dielectric Spectroscopy Data", Analytica Chimica Acta, vol. No. 628, Issue No. 1, pp. 117-120, Oct. 17, 2008.
Li et al., "Chemical Sensing Using Nanostructured Polythiophene Transistors", Nano Letters, vol. No. 8, Issue No. 11, pp. 3563-3567, Oct. 28, 2008.
Hwili et al., "A Single Rod Multi-Modality Multi-Interface Level Sensor using an AC Current Source", IEEE International Workshop on Imaging Systems and Techniques, Chania, Greece, pp. 1-5, Sep. 10-12, 2008.
Wudy et al., "Rapid Impedance Scanning QCM for Electrochemical Applications Based on Miniaturized Hardware and High-Performance Curve Fitting", Electrochimica Acta, vol. No. 53, Issue No. 22, pp. 6568-6574, Sep. 20, 2008.
Sweden Office Action issued in connection with related SE Application No. 0702495-3 dated Sep. 24, 2008.
Potyrailo et al., "RFID Sensors Based on Ubiquitous Passive 13.56-MHz RFID Tags and Complex Impedance Detection", Wireless Communications and Mobile Computing, pp. 1-13, Nov. 2008.
Saltas et al., "Dielectric Properties of Non-Swelling Bentonite: The Effect of Temperature and Water Saturation", Journal of Non-Crystalline Solids, vol. No. 354, Issue No. 52-54, pp. 5533-5541, Dec. 15, 2008.
Sacristan-Riquelme et al., "Low Power Impedance Measurement Integrated Circuit for Sensor Applications", Microelectronics Journal, vol. No. 40, Issue No. 1, pp. 177-184, Jan. 2009.

(56) References Cited

OTHER PUBLICATIONS

Ertl et al., "Interdigitated Impedance Sensors for Analysis of Biological Cells in Microfluidic Biochips", Elektrotechnik & Informationstechnik, vol. No. 126, Issue No. 1, pp. 47-50, Jan.-Feb. 2009.

Potyrailo et al., "Passive Radio Frequency Identification (RFID) Chemical Sensors for Homeland Security Applications", Wiley Handbook of Science and Technology for Homeland Security, pp. 1-12, Jun. 15, 2009.

Potyrailo et al., "Selective Detection of Chemical Species in Liquids and Gases Using Passive Radio-Frequency Identification (RFID) Sensors", IEEE Conference on Transducers, Denver, CO, USA, pp. 1650-1653, Jun. 21-25, 2009.

Sweden Office Action issued in connection with related SE Application No. 0702495-3 dated Jul. 29, 2009.

Potyrailo et al., "Combinatorial Screening of Polymeric Sensing Materials Using RFID Sensors", Journal of Combinatorial Chemistry, vol. No. 11, Issue No. 4, pp. 598-603, Jul.-Aug. 2009.

Jaworski et al., "On-line Measurement of Separation Dynamics in Primary Gas/Oil/Water Separators: Challenges and Technical Solutions—A review", Journal of Petroleum Science and Engineering, vol. No. 68, Issue No. 1-2, pp. 47-59, Sep. 2009.

McCann et al., "Recent Advances in Lateral Field Excited and Monolithic Spiral Coil Acoustic Transduction Bulk Acoustic Wave Sensor Platforms", Measurement Science and Technology, vol. No. 20, Issue No. 12, pp. 124001-1-124001-12, Oct. 2009.

Westafer et al., "Functionalization of High Frequency SAW RFID Devices for Ozone Dosimetry", IEEE Sensors Conference, pp. 1747-1752, Oct. 25-28, 2009.

Niedermayer et al., "Yet Another Precision Impedance Analyzer (YAPIA)—Readout Electronics for Resonating Sensors", Sensors and Actuators A: Physical, vol. No. 156, Issue No. 1, pp. 245-250, Nov. 2009.

Potyrailo et al., "Development of Radio-Frequency Identification Sensors Based on Organic Electronic Sensing Materials for Selective Detection of Toxic Vapors", Journal of Applied Physics, vol. No. 106, Issue No. 12, pp. 124902-1-124902-6, Dec. 2009.

Mortier et al., "Chemistry and Technology of Lubricants", Third Edition, Springer, pp. 1-560, 2010.

Cho et al., "Capacitive Sensor for Automotive Engine Oil Degradation using Wireless Network", International Symposium on Advanced Packaging Materials: Microtech, Cambridge, pp. 88-91, Feb. 28-Mar. 2, 2010.

PCT Search Report and Written Opinion issued in connection with related PCT Application No. PCT/SE2009/051346 dated Mar. 15, 2010.

U.S. Non-Final Rejection issued in connection with related U.S. Appl. No. 11/560,476 dated Apr. 5, 2010.

Potyrailo et al. "Integration of Passive Multivariable RFID Sensors into Single-Use Biopharmaceutical Manufacturing Components", IEEE International Conference on RFID, Orlando, Florida, pp. 1-7, Apr. 14-16, 2010.

Potyrailo et al., "Selective Quantitation of Vapors and their Mixtures using Individual Passive Multivariable RFID Sensors", IEEE International Conference on RFID, Orlando, Florida, pp. 22-28, Apr. 14-16, 2010.

Becher et al., "The Detection of Evaporating Hazardous Material Released from Moving Sources Using a Gas Sensor Network", Sensors and Actuators B: Chemical, vol. No. 146, Issue No. 2, pp. 513-520, Apr. 29, 2010.

Alexander et al., "Optimization of Interdigitated Electrode (IDE) Arrays for Impedance Based Evaluation of Hs 578T Cancer Cells", Journal of Physics: Conference Series, vol. No. 224, Issue No. 1, pp. 012134-1-012134-4, May 2010.

Bobrov et al., "The Effect of Clay and Organic Matter Content on the Dielectric Permittivity of Soils and Grounds at the Frequency Range from 10 MHz to 1 GHz", International Geoscience and Remote Sensing Symposium (IGARSS), pp. 4433-4435, Jul. 25-30, 2010.

Chen et al., "Based on ZigBee Wireless Sensor Network the Monitoring System Design for Production Process Toxic and Harmful Gas", International Conference on Computer, Mechatronics, Control and Electronic Engineering, vol. No. 4, pp. 425-428, Aug. 24-26, 2010.

Hong et al., "Development of a Micro Liquid-Level Sensor for Harsh Environments using a Periodic Heating Technique", Measurement Science and Technology, vol. No. 21, Issue No. 10, Sep. 2010.

Bianchi et al., "Model of an Interdigitated Microsensor to Detect and Quantify Cells Flowing in a Test Chamber", 6th Annual COMSOL Conference, Paris, pp. 1-5, Nov. 2010.

Wang et al., "Flexible Chemiresistor Sensors: Thin film Assemblies of Nanoparticles on a Polyethylene Terephthalate Substrate", Journal of Materials Chemistry, vol. No. 20, pp. 907-915, Dec. 15, 2010.

Suresh et al., "Piezoelectric Based Resonant Mass Sensor using Phase Measurement", Measurement, vol. No. 44, Issue No. 2, pp. 320-325, Feb. 2011.

De Vito et al., "Wireless Sensor Networks for Distributed Chemical Sensing: Addressing Power Consumption Limits with On-Board Intelligence", IEEE Sensors Journal, vol. No. 11, Issue No. 14, pp. 947-955, Apr. 2011.

Potyrailo et al., "Passive Multivariable Temperature and Conductivity RFID Sensors for Single-Use Biopharmaceutical Manufacturing Components", Biotechnology Progress, vol. No. 27, Issue No. 3, pp. 875-884, May 2, 2011.

Sen et al., "Evaluation of Sensor Arrays for Engine Oils Using Artificial Oil Alteration", Proceedings of SPIE 8066, Smart Sensors Actuators and MEMS, vol. No. 8066, pp. 1-7, May 5, 2011.

Owenier et al., "Dielectric Permittivity of Geologic Materials at Different Water Contents—Measurements with an Impedance Analyzer", 6th International Workshop on Advanced Ground Penetrating Radar (IWAGPR), Aachen, Germany, pp. 1-5, Jun. 22-24, 2011.

Guan et al.,"Application of Dielectric Spectroscopy for Engine Lubricating Oil Degradation Monitoring", Sensors and Actuators A: Physical, vol. No. 168, Issue No. 1, pp. 22-29, Jul. 2011.

U.S. Non-Final Rejection issued in connection with related U.S. Appl. No. 12/424,016 dated Jul. 12, 2011.

Potyrailo et al. "RFID Sensors as the Common Sensing Platform for Single-Use Biopharmaceutical Manufacturing", Measurement Science and Technology, vol. No. 22, Issue No. 8, pp. 082001-1-082001-17, Jul. 15, 2011.

Jaworski et al., "Measurements of Oil-Water Separation Dynamics in Primary Separation Systems Using Distributed Capacitance Sensors", Flow Measurement and Instrumentation, vol. No. 16, Issue No. 2-3, pp. 113-127, Apr.-Jun. 2005.

Cheung et al., "Impedance Spectroscopy Flow Cytometry: On-Chip Label-Free Cell Differentiation", Cytometry Part A, vol. No. 65, Issue No. 2, pp. 124-132, Jun. 2005.

Jang et al., "Chemical Sensors Based on Highly Conductive Poly(3,4-Ethylene-Dioxythiophene) Nanorods", Advanced Materials, vol. No. 17, Issue No. 13, pp. 1616-1620, Jul. 1, 2005.

Rakow et al., "Molecular Recognition and Discrimination of Amines with a Colorimetric Array", Angewandte Chemie, vol. No. 44, Issue No. 29, pp. 4528-4532, Jul. 18, 2005.

Zhang et al., "A Calorimetric Sensor Array for Organics in Water", Journal of the American Chemical Society, vol. No. 127, Issue No. 33, pp. 11548-11549, Aug. 2, 2005.

Chuang et al., "Embeddable Wireless Strain Sensor Based on Resonant RF Cavities", Review of Scientific Instruments, vol. No. 76, Issue No. 9, pp. 094703-094703-7, Sep. 2005.

Burnell et al., "Synthesis and Electrooptical Properties of Copolymers Derived from Phenol-Functionalized Telechelic Oligofluorenes", Macromolecules, vol. No. 38, Issue No. 26, pp. 10667-10677, Nov. 19, 2005.

Bang et al., "A Novel Electrochemical Detection Method for Aptamer Biosensors", Biosensors and Bioelectronics, vol. No. 21, Issue No. 6, pp. 863-870, Dec. 15, 2005.

Lange et al., "Measuring Biomolecular Binding Events with a Compact Disc Player Device", Angewandte Chemie International Edition, vol. No. 45, Issue No. 2, pp. 270-273, Dec. 23, 2005.

(56) References Cited

OTHER PUBLICATIONS

Locklin et al., "Effect of Morphology on Organic Thin Film Transistor Sensors", Analytical and Bioanalytical Chemistry, vol. No. 384, Issue No. 2, pp. 336-342, 2006.
Morris et al., "Wireless Sensor Array System for Combinatorial Screening of Sensor Materials", Materials Research Society Symposium Proceedings, vol. No. 894, pp. 0894-LL07-02.1-0894-LL07-02.6, 2006.
Lvovich et al., "Impedance Characterization of Industrial Lubricants", Electrochimica Acta, vol. No. 51, Issue No. 8-9, pp. 1487-1496, Jan. 20, 2006.
Yang et al., "Chemical Identification Using an Impedance Sensor Based on Dispersive Charge Transport", Applied Physics Letters, vol. No. 88, Issue No. 7, pp. 074104-1-074104-3, Feb. 2006.
Meng et al., "A Multi-Electrode Capacitance Probe for Phase Detection in Oil-Water Separation Processes: Design, Modelling and Validation", Measurement Science and Technology, vol. No. 17, Issue No. 4, pp. 881-894, Mar. 23, 2006.
Casanella et al., "Oil-water Interface Level Sensor Based on an Electrode Array", Proceedings of the IEEE Instrumentation and Measurement Technology Conference, Sorrento, Italy, pp. 710-713, Apr. 24-27, 2006.
Yang, "Sensors and Instrumentation for Monitoring and Control of Multi-Phase Separation", Measurement and Control, vol. No. 39, Issue No. 6, pp. 1-12, Jul. 1, 2006.
Pejcic et al., "Impedance Spectroscopy: Over 35 Years of Electrochemical Sensor Optimization", Electrochimica Acta, vol. No. 51, Issue No. 28, pp. 6217-6229, Sep. 15, 2006.
Benini et al., "Wireless Sensor Networks: Enabling Technology for Ambient Intelligence", Microelectronics Journal, vol. No. 37, Issue No. 12, pp. 1639-1649, Dec. 2006.
Potyrailo et al., "Multianalyte Chemical Identification and Quantitation Using a Single Radio Frequency Identification Sensor", Analytical Chemistry, vol. No. 79, Issue No. 1, pp. 45-51, 2007.
Li et al., "Chemosensory Performance of Molecularly Imprinted Fluorescent Conjugated Polymer Materials", Journal of the American Chemical Society, vol. No. 129, Issue No. 51, pp. 15911-15918, 2007.
Wang et al., "Array of Molecularly Mediated Thin Film Assemblies of Nanoparticles: Correlation of Vapor Sensing with Interparticle Spatial Properties", Journal of the American Chemical Society, vol. No. 129, Issue No. 7, pp. 2161-2170, 2007.
Hewitt, "Oil/Water Interface Control for Desalters", Petroleum Technology Quarterly, vol. No. 12, Issue No. 5, pp. 75-78, 2007.
Hwili et al., "Multi-Modality Multi-Interface Level Measurement", Journal of Physics: Conference Series, vol. No. 76, Issue No. 1, pp. 1-6, 2007.
Hempel et al., "Application of a Portable RF Impedance Spectrum Analyzer for the Investigation of Lateral Field Excited Acoustic Wave Sensors in a Liquid Environment", Ultrasonics Symposium Proceeding, vol. No. 1, pp. 373-376, Jan. 1, 2007.
Hwang et al., "Photoelectron Spectroscopic Study of the Electronic Band Structure of Polyfluorene and Fluorene-Arylamine Copolymers at Interfaces", The Journal of Physical Chemistry C, vol. No. 111, Issue No. 3, pp. 1378-1384, Jan. 2007.
Qing et al., "RFID Tag Antennas", Antennas for Portable Devices, John Wiley & Sons, Ltd, pp. 59-61; 65-69, Mar. 2007.
Bai et al., "Gas Sensors Based on Conducting Polymers", Sensors, vol. No. 7, Issue No. 3, pp. 267-307, Mar. 2007.
Gutzeit, "Controlling Crude Unit Overhead Corrosion—Rules of Thumb for Better Crude Desalting", NACE International Corrosion Conference & Expo, Nashville, Tennessee, pp. 1-21, Mar. 11-15, 2007.
Casanella et al., "Continuous Liquid Level Measurement Using a Linear Electrode Array", Measurement Science and Technology, vol. No. 18, Issue No. 7, pp. 1859-1866, May 9, 2007.
Metzger et al., "Weight-Sensitive Foam to Monitor Product Availability on Retail Shelves", 5th International Conference on Pervasive Computing, Toronto, Canada, vol. No. 4480, pp. 268-279, May 13-16, 2007.
Li et al., "Inkjet Printed Chemical Sensor Array Based on Polythiophene Conductive Polymers", Sensors and Actuators B: Chemical, vol. No. 123, Issue No. 2, pp. 651-660, May 21, 2007.
Liu et al., "Measurement of Density and Viscosity of Dodecane and Decane with a Piezoelectric Tuning Fork Over 298-448 K and 0.1-137.9 MPa", Sensors and Actuators A Physical, vol. No. 167, Issue No. 2, pp. 347-353, Jun. 2007.
Lu et al., "MEMS-Based Inductively Coupled RFID Transponder for Implantable Wireless Sensor Applications", IEEE Transactions on Magnetics, vol. No. 43, Issue No. 6, pp. 2412-2414, Jun. 2007.
Wei et al., "Simple and Sensitive Aptamer-Based Colorimetric Sensing of Protein using Unmodified Gold Nanoparticle Probes", Chemical Communications, Issue 36, pp. 3735-3737, Jun. 29, 2007.
Potyrailo et al., "Wireless Resonant Sensor Array for High-Throughput Screening of Materials", Review of Scientific Instruments, vol. No. 78, Issue No. 7, pp. 072214-1-072214-6, Jul. 2007.
Sugiyasu et al., "Conducting-Polymer-Based Chemical Sensors: Transduction Mechanisms", Bulletin of the Chemical Society of Japan, vol. No. 80, Issue No. 11, pp. 2074-2083, Aug. 2007.
Armani et al., "Label-Free Single-Molecule Detection with Optical Microcavities", Science, vol. No. 317, Issue No. 5839, pp. 783-787, Aug. 10, 2007.
Tan et al., "A Wireless, Passive Sensor for Quantifying Packaged Food Quality", Sensors, vol. No. 7, Issue No. 9, pp. 1747-1756, Sep. 2007.
Wang et al., "A New Method for On-line Monitoring of Brake Fluid Condition using an Enclosed Reference Probe", Measurement Science and Technology, vol. No. 18, Issue No. 11, pp. 3625-3635, Oct. 16, 2007.
Wang et al., "A Gold Nanoparticle-Based Aptamer Target Binding Readout for ATP Assay", Advanced Materials, vol. No. 19, Issue No. 22, pp. 3943-3946, Nov. 2007.
Tanaka et al., "Quartz Crystal Capacitive Sensor with Inductance-Capacitance Resonance Circuit for Vapor Sensing", Japanese Journal of Applied Physics, vol. No. 46, Issue No. 11, pp. 7509-7511, Nov. 2007.
Ulrich et al., "Simultaneous Estimation of Soot and Diesel Contamination in Engine Oil Using Electrochemical Impedance Spectroscopy", Sensors and Actuators B: Chemical, vol. No. 127, Issue No. 2, pp. 613-618, Nov. 15, 2007.
Husebo, "Ultrasonic Interface Level Detector", Christian Michelsen Research AS, pp. 1-2, 2008.
Surman et al., "Quantitation of Toxic Vapors in Variable Humidity Atmosphere Using Individual Passive Radio Frequency Identification (RFID) Sensors", 12th International Meeting on Chemical Sensors, Columbus, pp. 1-2, 2008.
Potyrailo et al., "Modeling of Selectivity of Multi-Analyte Response of Passive Radio Frequency Identification (RFID) Sensors", 12th International Meeting on Chemical Sensors, Columbus, pp. 1-3, 2008.
Wang et al., "Sensors and Biosensors for the Determination of Small Molecule Biological Toxins", Sensors, vol. No. 8, Issue No. 9, pp. 6045-6054, 2008.
Jimenez et al., "Surface Characterization of Clay Particles via Dielectric Spectroscopy", Annales Universitatis Mariae Curie-Sklodowska, vol. No. 63, Issue No. 1, pp. 73-86, Jan. 2008.
Metzger et al., "Flexible-Foam-Based Capacitive Sensor Arrays for Object Detection at Low Cost", Applied Physics Letters, vol. No. 92, Issue No. 1, pp. 013506-1-013506-3, Jan. 2008.
Hatchett et al., "Composites of Intrinsically Conducting Polymers as Sensing Nanomaterials", Chemical Reviews, vol. No. 108, Issue No. 2, pp. 746-769, Jan. 3, 2008.
Joo et al., "Chemical Sensors with Integrated Electronics", Chemical Reviews, vol. No. 108, Issue No. 2, pp. 638-651, Jan. 10, 2008.
Bret Dwayne Worden et al., filed Feb. 12, 2015, U.S. Appl. No. 14/421,245.
Radislav Alexandrovich Potyrailo et al., filed Nov. 16, 2006, U.S. Appl. No. 11/560,476.
Cheryl Margaret Surman et al., filed Jun. 28, 2010, U.S. Appl. No. 12/824,436.
Radislav Alexandrovich Potyrailo et al., filed Dec. 23, 2010, U.S. Appl. No. 12/977,568.

(56) References Cited

OTHER PUBLICATIONS

Radislav Alexandrovich Potyrailo et al., filed Dec. 20, 2011, U.S. Appl. No. 13/331,003.
Radislav Alexandrovich Potyrailo et al., filed Jun. 29, 2012, U.S. Appl. No. 13/538,570.
Radislav Alexandrovich Potyrailo et al., filed Jul. 26, 2012, U.S. Appl. No. 13/558,499.
Radislav Alexandrovich Potyrailo et al., filed Sep. 28, 2012, U.S. Appl. No. 13/630,939.
Radislav Alexandrovich Potyrailo et al., filed Dec. 28, 2012, U.S. Appl. No. 13/729,800.
Radislav Alexandrovich Potyrailo et al., filed Dec. 28, 2012, U.S. Appl. No. 13/729,851.
Radislav Alexandrovich Potyrailo et al., filed Nov. 9, 2010, U.S. Appl. No. 12/942,732.
Radislav Alexandrovich Potyrailo et al., filed Dec. 23, 2010, U.S. Appl. No. 12/977,599.
GB Office Action issued in connection with related GB Application No. GB1121548.0 dated Aug. 24, 2016.
Wang et al., "Impedance Analysis for Lateral Field Excited Acoustic Wave Sensors", Sensors and Actuators B: Chemical, vol. No. 156, Issue No. 2, pp. 969-975, Aug. 2011.
Latif et al., "Conductometric Sensors for Monitoring Degradation of Automotive Engine Oil", Sensors, vol. No. 11, Issue No. 9, pp. 8611-8625, Sep. 5, 2011.
Potyrailo et al., "Materials and Transducers Toward Selective Wireless Gas Sensing", Chemical Reviews, vol. No. 111, Issue No. 11, pp. 7315-7354, Sep. 7, 2011.
PCT Search Report and Written Opinion issued in connection with related PCT Application No. PCT/SE2011/050748 dated Oct. 5, 2011.
PCT Search Report and Written Opinion issued in connection with related PCT Application No. PCT/SE2011/050818 dated Oct. 24, 2011.
Perez et al., "Low-Cost Oil Quality Sensor Based on Changes in Complex Permittivity", Sensors, vol. No. 11, Issue No. 11, pp. 10675-10690, Nov. 2011.
Potyrailo et al., "Multivariable Passive RFID Vapor Sensors: Pilot-Scale Manufacturing and Laboratory Evaluation", Future of Instrumentation International Workshop, pp. 1-2, Nov. 7-8, 2011.
Aghayan, "On-Line Monitoring of Engine Health through the Analysis of Contaminants in Engine Lubricant", The School of Graduate and Postdoctoral Studies, The University of Western Ontario, London, Ontario, Canada, pp. 1-273, 2012.
Potyrailo et al., "Multivariable MHz and GHz Wireless Chem/Bio Sensors for Environmental, Industrial, and Security Applications", The 14th International Meeting on Chemical Sensors, Nuremberg, Germany, pp. 399-402, May 20-23, 2012.
Vasilyeva et al., "Differences in Behaviour of Adsorbed Water in Kaolinites and Montmorillonites in Temperature Range from −90° C. to +140° C. by Dielectric Spectroscopy", Journal of Physics: Conference Series, vol. No. 394, Issue No. 1, pp. 012028-1-012028-6, 2012.
Datla et al., "Wireless Distributed Computing: A Survey of Research Challenges", IEEE Communications Magazine, vol. No. 50, Issue No. 1, pp. 144-152, Jan. 5, 2012.
Combined GB Search and Examination Report issued in connection with related GB Application No. GB1121548.0 dated Mar. 28, 2012.
Datla et al., "Wireless Distributed Computing in Cognitive Radio Networks", Ad Hoc Networks, vol. No. 10, Issue No. 05, pp. 845-857, Jul. 2012.
U.S. Non-Final Rejection issued in connection with related U.S. Appl. No. 11/560,476 dated Jul. 5, 2012.
Fochtmann et al., "Optimization of the Lateral Field Excited Platform for Liquid Sensing Applications", Sensors and Actuators B: Chemical, vol. No. 170, pp. 95-103, Jul. 31, 2012.
Japanese Office Action issued in connection with related JP Application No. 2007291481 dated Aug. 7, 2012.
U.S. Non-Final Rejection issued in connection with related U.S. Appl. No. 12/824,436 dated Aug. 8, 2012.
Chinese Office Action issued in connection with related CN Application No. 200980149087.6 dated Sep. 13, 2012.
U.S. Notice of Allowance issued in connection with related U.S. Appl. No. 12/424,016 dated Sep. 28, 2012.
U.S. Non-Final Rejection issued in connection with related U.S. Appl. No. 12/325,653 dated Nov. 16, 2012.
U.S. Non-Final Rejection issued in connection with related U.S. Appl. No. 12/977,599 dated Feb. 5, 2013.
U.S. Final Rejection issued in connection with related U.S. Appl. No. 12/824,436 dated Feb. 6, 2013.
U.S. Non-Final Rejection issued in connection with related U.S. Appl. No. 12/942,732 dated Feb. 7, 2013.
De Souza et al., "A Close Dielectric Spectroscopic Analysis of Diesel/Biodiesel Blends and Potential Dielectric Approaches for Biodiesel Content Assessment", Fuel, vol. No. 105, pp. 705-710, Mar. 2013.
Japanese Notice of Allowance issued in connection with related JP Application No. 2007291481 dated Mar. 5, 2013.
Swiech et al., "Dielectric Properties of Synthetic Oil Sands", Society of Petroleum Engineers—SPE Heavy Oil Conference, Calgary, Alberta, Canada, vol. No. 1, pp. 1-11, Jun. 11-13, 2013.
Zhu et al., "Survey of Lubrication Oil Condition Monitoring, Diagnostics, and Prognostics Techniques and Systems", Journal of Chemical Science and Technology, vol. No. 2, Issue No. 3, pp. 100-115, Jul. 2013.
U.S. Final Rejection issued in connection with related U.S. Appl. No. 12/325,653 dated Aug. 8, 2013.
Agilent Impedance Measurement Handbook, "A Guide to Measurement Technology and Techniques", 4th Edition, Agilent Technologies, pp. 1-140, Sep. 10, 2013.
Japanese Office Action issued in connection with related JP Application No. 2011538590 dated Oct. 8, 2013.
PCT Search Report and Written Opinion issued in connection with related PCT Application No. PCT/SE2013/050671 dated Nov. 18, 2013.
PCT Search Report and Written Opinion issued in connection with related PCT Application No. PCT/US2013/058932 dated Dec. 12, 2013.
PCT Search Report and Written Opinion issued in connection with related PCT Application No. PCT/US2013/058898 dated Dec. 18, 2013.
Chinese Office Action issued in connection with related CN Application No. 201180031959.6 dated Dec. 26, 2013.
U.S. Non-Final Rejection issued in connection with related U.S. Appl. No. 12/977,568 dated Jan. 16, 2014.
PCT Search Report and Written Opinion issued in connection with related PCT Application No. PCT/US2012/070448 dated Jan. 27, 2014.
PCT Search Report and Written Opinion issued in connection with related PCT Application No. PCT/US2013/055983 dated Jan. 27, 2014.
U.S. Non-Final Rejection issued in connection with related U.S. Appl. No. 12/827,623 dated Jan. 30, 2014.
European Search Report and Opinion issued in connection with related EP Application No. 11801238.4 dated Mar. 5, 2014.
Toledo et al., "Application of Quartz Tuning Forks and Extensional Microresonators for Viscosity and Density Measurements in Oil/Fuel Mixtures", Microsystem Technologies, vol. No. 20, Issue No. 4, pp. 945-953, Apr. 2014.
PCT Search Report and Written Opinion issued in connection with related PCT Application No. PCT/SE2013/051589 dated May 6, 2014.
PCT Search Report and Written Opinion issued in connection with related PCT Application No. PCT/SE2013/051590 dated May 6, 2014.
Elzagzoug et al., "Condition Monitoring of High Voltage Transformer Oils Using Optical Chromaticity", Measurement Science and Technology, vol. No. 25, Issue No. 6, pp. 065205-1-065205-9, Jun. 2014.
Soleimani et al., "Base Oil Oxidation Detection Using Novel Chemical Sensors and Impedance Spectroscopy Measurements", Sensors and Actuators B: Chemical, vol. No. 199, pp. 247-258, Aug. 2014.

(56) References Cited

OTHER PUBLICATIONS

U.S. Non-Final Rejection issued in connection with related U.S. Appl. No. 13/630,939 dated Aug. 11, 2014.
U.S. Non-Final Rejection issued in connection with related U.S. Appl. No. 14/031,965 dated Aug. 26, 2014.
U.S. Non-Final Rejection issued in connection with related U.S. Appl. No. 14/031,951 dated Sep. 2, 2014.
U.S. Non-Final Rejection issued in connection with related U.S. Appl. No. 13/331,003 dated Sep. 10, 2014.
U.S. Final Rejection issued in connection with related U.S. Appl. No. 12/325,653 dated Sep. 12, 2014.
U.S. Non-Final Rejection issued in connection with related U.S. Appl. No. 13/484,674 dated Nov. 3, 2014.
Bauerle, "Study of Solid Electrolyte Polarization by a Complex Admittance Method", Journal of Physics and Chemistry of Solids, vol. No. 30, Issue No. 12, pp. 2657-2670, Dec. 1969.
Matsui, "Complex-Impedance Analysis for the Development of Zirconia Oxygen Sensors", Solid State Ionics, vol. No. 3-4, pp. 525-529, Aug. 1981.
Persaud et al., "Analysis of Discrimination Mechanisms in the Mammalian Olfactory System Using a Model Nose", Nature, vol. No. 299, pp. 352-355, Sep. 23, 1982.
Sen et al., "The Frequency Dependent Dielectric and Conductivity Response of Sedimentary Rocks", Journal of Microwave Power, vol. No. 18, Issue No. 1, pp. 95-105, 1983.
Raythatha et al., "Dielectric Properties of Clay Suspensions in MHz to GHz Range", Journal of Colloid and Interface Science, vol. No. 109, Issue No. 2, pp. 301-309, Feb. 1986.
Ward et al., "In Situ Interfacial Mass Detection with Piezoelectric Transducers", Science, vol. No. 249, Issue No. 4972, pp. 1000-1007, Aug. 31, 1990.
Shi et al., "Capacitance-Based Instrumentation for Multi-Interface Level Measurement", Measurement Science and Technology, vol. No. 2, Issue No. 10, pp. 923-933, May 17, 1991.
Gutierrez et al., "Use of Complex Impedance Spectroscopy in Chemical Sensor Characterization", Sensors and Actuators B: Chemical, vol. No. 4, Issue No. 3-4, pp. 359-363, Jun. 1991.
Wise et al., "Microfabrication Techniques for Integrated Sensors and Microsystems", Science, vol. No. 254, pp. 1335-1342, Nov. 29, 1991.
Mullen et al., "Trace Detection of Ionic Species with Surface Enhanced Raman Spectroscopy", Spectroscopy, vol. No. 7, Issue No. 5, pp. 24-32, Jun. 1992.
Ervin et al., "Development of a Fiber-Optic Sensor for Trace Metal Detection in Aqueous Environments", Applied Optics, vol. No. 32, Issue No. 22, pp. 4287-4290, Aug. 1, 1993.
Agar et al., "Energy Absorption Probes Control Oily-Water Discharges", Hydrocarbon Processing, vol. No. 72, Issue No. 8, pp. 55-59, Aug. 1, 1993.
Wensink, "Dielectric Properties of Wet Soils in the Frequency Range 1-3000 MHz", Geophysical Prospecting, vol. No. 41, Issue No. 6, pp. 671-696, Aug. 1993.
Pal, "Techniques for Measuring the Composition (Oil and Water Content) of Emulsions—A state of the Art Review", Colloids and Surfaces: A Physicochemical and Engineering Aspects, vol. No. 84, Issue No. 2-3, pp. 141-193, May 11, 1994.
Garrouch et al., "The Influence of Clay Content, Salinity, Stress, and Wettability on the Dielectric Properties of Brine-Saturated Rocks: 10 Hz to 10 MHz", Geophysics, vol. No. 59, Issue No. 6, pp. 909-917, Jun. 1994.
Isaksen et al., "A Capacitance-Based Tomography System for Interface Measurement in Separation Vessels", Measurement Science and Technology, vol. No. 5, Issue No. 10, pp. 1262-1271, Jun. 9, 1994.
Yang et al., "A Multi-Interface Level Measurement System using a Segmented Capacitance Sensor for Oil Separators", Measurement Science and Technology, vol. No. 5, Issue No. 9, pp. 1177-1180, Jul. 19, 1994.

Garcia-Golding et al., "Sensor for Determining the Water Content of Oil-in-water Emulsion by Specific Admittance Measurement", Sensors and Actuators: A. Physical, vol. No. 47, Issue No. 1-3, pp. 337-341, Mar.-Apr. 1995.
Ghiotti et al., "Moisture Effects on Pure and Pd-Doped SnO2 Thick Films Analysed by FTIR Spectroscopy and Conductance Measurements", Sensors and Actuators B: Chemical, vol. No. 25, Issue No. 1-3, pp. 520-524, Apr. 1995.
Legin et al., "Development and Analytical Evaluation of a Multisensor System for Water Quality Monitoring", Sensors and Actuators B: Chemical, vol. No. 27, Issue No. 1-3, pp. 377-379, Jun. 1995.
Malinowska et al., "Enhanced Electrochemical Performance of Solid-State Ion Sensors Based on Silicone Rubber Membranes", The 8th International Conference on Solid-State Sensors and Actuators, and Eurosensors IX, Stockholm, Sweden, pp. 851-854, Jun. 25-29, 1995.
Amrani et al., "High-Frequency Measurements of Conducting Polymers: Development of a New Technique for Sensing Volatile Chemicals", Measurement Science and Technology, vol. No. 6, Issue No. 10, pp. 1500-1507, Jul. 20, 1995.
Hutzler et al., "Measurement of Foam Density Profiles Using AC Capacitance", Europhysics Letters, vol. No. 31, Issue No. 8, pp. 497-502, Sep. 10, 1995.
Nicolaou et al., "Radiofrequency Encoded Combinatorial Chemistry", Angewandte Chemie International Edition, vol. No. 34, Issue No. 20, pp. 2289-2291, Nov. 3, 1995.
Leff et al., "Synthesis and Characterization of Hydrophobic, Organically-Soluble Gold Nanocrystals Functionalized with Primary Amines", Langmuir, vol. No. 12, Issue No. 20, pp. 4723-4730, 1996.
Amrani et al., "Multi-Frequency Measurements of Organic Conducting Polymers for Sensing of Gases and Vapours", Sensors and Actuators B: Chemical, vol. No. 33, Issue No. 1-3, pp. 137-141, Jul. 1996.
Di Natale et al., "Multicomponent Analysis of Heavy Metal Cations and Inorganic Anions in Liquids by a Non-Selective Chalcogenide Glass Sensor Array", Sensors and Actuators B: Chemical, vol. No. 34, Issue No. 1-3, pp. 539-542, Aug. 1996.
Chinowsky et al., "Experimental Data from a Trace Metal Sensor Combining Surface Plasmon Resonance with Anodic Stripping Voltammetry", Sensors and Actuators B: Chemical, vol. No. 35, Issue No. 1-3, pp. 37-43, Sep. 1996.
Josse et al., "AC-Impedance-Based Chemical Sensors for Organic Solvent Vapors", Sensors and Actuators B: Chemical, vol. No. 36, Issue No. 1-3, pp. 363-369, Oct. 1996.
Santamarina et al., "Dielectric Permittivity of Soils Mixed With Organic and Inorganic Fluids (0.02GHz to 1.30 GHz)", Journal of Environmental and Engineering Geophysics, vol. No. 2, Issue No. 1, pp. 37-51, Mar. 1997.
Wang et al., "The Application of A.C. Impedance Technique for Detecting Glycol Contamination in Engine Oil", Sensors and Actuators B: Chemical, vol. No. 40, Issue No. 2-3, pp. 193-197, May 15, 1997.
Hammond et al., "An Acoustic Automotive Engine Oil Quality Sensor", International Conference on Solid-State Sensors and Actuators, Chicago, pp. 1343-1346, Jun. 16-19, 1997.
Amrani et al., "An Intelligent Gas Sensing System", Sensors and Actuators B: Chemical, vol. No. 44, Issue No. 1-3, pp. 512-516, Oct. 1997.
Di Natale et al., "Multicomponent Analysis on Polluted Waters by Means of an Electronic Tongue", Sensors and Actuators B: Chemical, vol. No. 44, Issue No. 1-3, pp. 423-428, Oct. 1997.
Vlasov et al., "Cross-Sensitivity Evaluation of Chemical Sensors for Electronic Tongue: Determination of Heavy Metal Ions", Sensors and Actuators B: Chemical, vol. No. 44, Issue No. 1-3, pp. 532-537, Oct. 1997.
Ehret et al., "On-line Control of Cellular Adhesion with Impedance Measurements Using Interdigitated Electrode Structures", Medical & Biological Engineering & Computing, vol. No. 36, Issue No. 3, pp. 365-370, May 1998.
Wohltjen et al., "Colloidal Metal-Insulator-Metal Ensemble Chemiresistor Sensor", Analytical Chemistry, vol. No. 70, Issue No. 14, pp. 2856-2859, Jul. 15, 1998.

(56) References Cited

OTHER PUBLICATIONS

Jaworski et al., "A Capacitance Probe for Interface Detection in Oil and Gas Extraction Plant", Measurement of Science and Technology, vol. No. 10, Issue No. 3, pp. L15-L20, Jan. 1999.

Homola et al., "Surface Plasmon Resonance Sensors: Review", Sensors and Actuators B: Chemical, vol. No. 54, Issue No. 1-2, pp. 3-15, Jan. 25, 1999.

Amrani et al., "Multi-Frequency Interrogation Technique Applied to Conducting Polymer Gas and Odour Sensors", IEE Proceedings—Science, Measurement and Technology, vol. No. 146, Issue No. 2, pp. 95-101, Mar. 1999.

Ishida et al., "Effects of pH on Dielectric Relaxation of Montmorillonite, Allophane, and Imogolite Suspensions", Journal of Colloid and Interface Science, vol. No. 212, Issue No. 1, pp. 152-161, Apr. 1, 1999.

Asskildit et al., "New Measuring Sensor for Level Detection in Subsea Separators", ABB Review, pp. 11-17, Apr. 1999.

Schuller et al., "Advanced Profile Gauge for Multiphase Systems", 1st World Congress on Industrial Process Tomography, Buxton, Greater Manchester, pp. 126-132, Apr. 14-17, 1999.

Legin et al., "The Features of the Electronic Tongue in Comparison with the Characterstics of the Discrete Ion-Selective Sensors", Sensors and Actuators B: Chemical, vol. No. 58, Issue No. 1-3, pp. 464-468, Sep. 21, 1999.

Artmann, "Electronic Identification Systems: State of the Art and their Further Development", Computers and Electronics in Agriculture, vol. No. 24, Issue No. 1-2, pp. 5-26, Nov. 1999.

Chyan et al., "Ultrapure Water Quality Monitoring by a Silicon-Based Potentiometric Sensor", Analyst, vol. No. 125, Issue No. 1, pp. 175-178, 2000.

Basu et al., ""Smart Sensing" of Oil Degradation and Oil Level Measurements in Gasoline Engines", SAE 2000 World Congress, Detroit, Michigan, 2000-01-1366, pp. 1-7, Mar. 6-9, 2000.

Jurs et al., "Computational Methods for the Analysis of Chemical Sensor Array Data from Volatile Analytes", Chemical Reviews, vol. No. 100, Issue No. 7, pp. 2649-2678, Jun. 7, 2000.

McQuade et al., "Conjugated Polymer-Based Chemical Sensors", Chemical Reviews, vol. No. 100, Issue No. 7, pp. 2537-2574, Jun. 9, 2000.

Vlasov et al., "«Electronic Tongue»—New Analytical Tool for Liquid Analysis on the basis of Non-Specific Sensors and Methods of Pattern Recognition", Sensors and Actuators B: Chemical, vol. No. 65, Issue No. 1-3, pp. 235-236, Jun. 30, 2000.

Hendrick, "Cellulose Acetate Fibers with Fluorescing Nanoparticles for Anti-Counterfeiting Purposes", Erin Sue Hendrick, pp. 1-36, 2008.

Surman et al., "Data Processing in Multivariable RFID Vapor Sensors", IEEE Future of Instrumentation International Workshop (FIIW), pp. 28-31, 2011.

U.S. Notice of Allowance issued in connection with Related U.S. Appl. No. 13/838,884 dated Nov. 20, 2015.

Chinese Office Action issued in connection with related CN Application No. 201280070165.5 dated Jul. 13, 2016.

U.S. Notice of Allowance issued in connection with Related U.S. Appl. No. 13/538,570 dated Nov. 7, 2016.

Japanese Search Report issued in connection with related JP Application No. 2011258627 dated Dec. 1, 2016.

European Search Report issued in connection with related EP Application No. 16191069.0 dated Jan. 30, 2017.

U.S. Non-Final Rejection issued in connection with related U.S. Appl. No. 13/558,499 dated Dec. 4, 2014.

U.S. Non-Final Rejection issued in connection with related U.S. Appl. No. 13/630,954 dated Dec. 15, 2014.

U.S. Non-Final Rejection issued in connection with related U.S. Appl. No. 13/729,800 dated Dec. 19, 2014.

U.S. Final Rejection issued in connection with related U.S. Appl. No. 13/630,939 dated Jan. 28, 2015.

Hoja et al., "Miniaturized Impedance Analyzer Using AD5933", Lecture Notes on Impedance Spectroscopy, vol. No. 5, pp. 93-100, Feb. 17, 2015.

U.S. Non-Final Rejection issued in connection with related U.S. Appl. No. 13/630,739 dated Feb. 25, 2015.

Chinese Office Action issued in connection with related CN Application No. 201180032850.4 dated Mar. 2, 2015.

U.S. Final Rejection issued in connection with related U.S. Appl. No. 12/824,436 dated Mar. 5, 2015.

Chabowski et al., "Simple Wide Frequency Range Impedance Meter Based on AD5933 Integrated Circuit", Metrology and Measurement Systems, vol. No. 22, Issue No. 1, pp. 13-24, Mar. 15, 2015.

Japanese Office Action issued in connection with related JP Application No. 2013518325 dated Mar. 24, 2015.

Chinese Office Action issued in connection with related CN Application No. 201110461799.0 dated Mar. 30, 2015.

Japanese Office Action issued in connection with related JP Application No. 2013518328 dated Apr. 7, 2015.

SIMIC, "Complex Impedance Measurement System for the Frequency Range from 5 kHz to 100 kHz", Key Engineering Materials, vol. No. 644, pp. 133-136, May 11, 2015.

U.S. Non-Final Rejection issued in connection with related U.S. Appl. No. 13/630,587 dated Jun. 2, 2015.

U.S. Final Rejection issued in connection with related U.S. Appl. No. 13/630,739 dated Jun. 4, 2015.

European Search Report and Opinion issued in connection with related EP Application No. 11801234.3 dated Jun. 10, 2015.

U.S. Non-Final Rejection issued in connection with related U.S. Appl. No. 13/838,884 dated Jun. 17, 2015.

Chen et al., "Novel Undercoupled Radio-Frequency (RF) Resonant Sensor for Gaseous Ethanol and Interferents Detection", Sensors and Actuators A: Physical, vol. No. 230, pp. 63-73, Jul. 1, 2015.

PCT Search Report and Written Opinion issued in connection with related PCT Application No. PCT/US2015/027482 dated Jul. 15, 2015.

U.S. Notice of Allowance issued in connection with related U.S. Appl. No. 13/558,499 dated Jul. 27, 2015.

Japanese Notice of Allowance issued in connection with related JP Application No. 2011258627 dated Aug. 4, 2015.

Taiwan Office Action issued in connection with related TW Application No. 100146015 dated Aug. 6, 2015.

U.S. Non-Final Rejection issued in connection with related U.S. Appl. No. 13/630,939 dated Sep. 14, 2015.

Japanese Decision to Grant of Patent issued in connection with related JP Application No. 2013518325 dated Sep. 15, 2015.

Ghaffari et al., "A Wireless Multi-Sensor Dielectric Impedance Spectroscopy Platform", Sensors, vol. No. 15, Issue No. 9, pp. 23572-23588, Sep. 17, 2015.

U.S. Non-Final Rejection issued in connection with related U.S. Appl. No. 13/538,570 dated Oct. 22, 2015.

European Search Report and Opinion issued in connection with related EP Application No. 11801234.3 dated Oct. 28, 2015.

Wang et al., "Probe Improvement of Inductive Sensor for Online Health Monitoring of Mechanical Transmission Systems", IEEE Transactions on Magnetics, vol. No. 51, Issue No. 11, pp. 1-4, Nov. 2015.

Chinese Office Action issued in connection with related CN Application No. 201380043615.6 dated Nov. 9, 2015.

U.S. Non-Final Rejection issued in connection with related U.S. Appl. No. 12/824,436 dated Dec. 2, 2015.

Poseidon Systems, "Oil Quality Products", TRIDENT QM1100; TRIDENT QM2100; TRIDENT WM800, pp. 1-3, Retrieved from http://www.poseidonsys.com/products/oil-quality on Dec. 24, 2015.

Tandelta Systems, "Oil Quality Sensor", Tandelta Oil Condition Monitoring, pp. 1-5, Retrieved from http://www.tandeltasystems.com/products/oil-quality-sensor-2/ on Dec. 24, 2015.

Zhu et al. "An Integrated Lubricant Oil Conditioning Sensor Using Signal Multiplexing", Journal of Micromechanics and Microengineering, vol. No. 25, Issue No. 1, pp. 015006-1-015006-12, Dec. 24, 2015.

Unofficial English Translation of Japanese Notice of Allowance issued in connection with related JP Application No. 2013518328 dated Jan. 19, 2016.

Chinese Office Action issued in connection with related CN Application No. 201380050788.0 dated Jan. 20, 2016.

(56) References Cited

OTHER PUBLICATIONS

PCT Search Report and Written Opinion issued in connection with related PCT Application No. PCT/EP2015/075026 dated Feb. 1, 2016.
GB Office Action issued in connection with related GB Application No. GB1121548.0 dated Feb. 10, 2016.
Chinese Office Action issued in connection with related CN Application No. 201380050847.4 dated Feb. 29, 2016.
U.S. Notice of Allowance issued in connection with related U.S. Appl. No. 13/538,570 dated Mar. 1, 2016.
U.S. Final Rejection issued in connection with related U.S. Appl. No. 12/824,436 dated Apr. 25, 2016.
Chinese Office Action issued in connection with related CN Application No. 201380050788.0 dated Jun. 1, 2016.
AU Examination Report issued in connection with related AU Application No. 2013305814 dated Jun. 10, 2016.
U.S. Notice of Allowance issued in connection with related U.S. Appl. No. 13/538,570 dated Jun. 15, 2016.
U.S. Non-Final Rejection issued in connection with related U.S. Appl. No. 15/175,127 dated Jul. 29, 2016.
Ex Parte Quayle Action issued in connection with related U.S. Appl. No. 14/532,168 on Aug. 4, 2016.
Eurasian Search Report issued in connection with related EA Application No. 201592216 dated Aug. 4, 2016.
European Search Report and Opinion issued in connection with related EP Application No. 13866949.4 dated Aug. 8, 2016.
European Search Report and Opinion issued in connection with related EP Application No. 13867012.0 dated Aug. 9, 2016.
U.S. Non-Final Rejection issued in connection with related U.S. Appl. No. 14/710,299 dated Aug. 29, 2016.
U.S. Non-Final Rejection issued in connection with related U.S. Appl. No. 12/824,436 dated Sep. 6, 2016.
Examination Report No. 1 issued in connection with corresponding AU Application No. 2016228266 dated Jul. 7, 2017.
Worden, B.D., Gear Case Health Sensor, GE Co-Pending U.S. Appl. No. 61/692,230, filed Aug 22, 2012.
Worden, B., et al., System and Method for Utilizing Vehicle Sensor Information, GE Co-Pending U.S. Appl. No. 62/269,192, filed Dec. 18, 2015.
Worden, B., et al., Sensor Signal Processing System and Method, GE Co-Pending U.S. Appl. No. 62/269,304, filed Dec. 18, 2015.
Machine Translation and First Office Action and Search issued in connection with corresponding CN Application No. 201610865645.0 dated Dec. 20, 2018.
Office Action issued in connection with corresponding EP Application No. 16 191 069.0-1001 dated Mar. 22, 2019.

* cited by examiner

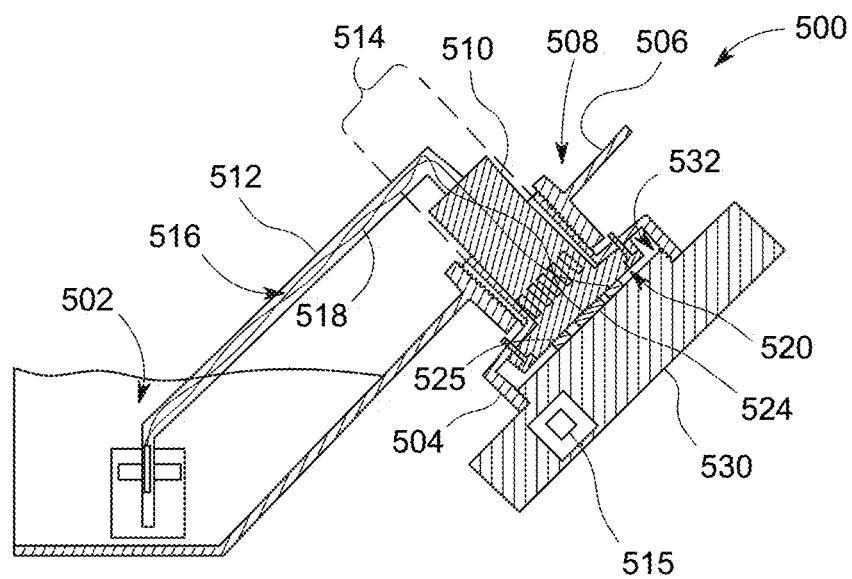
FIG. 11
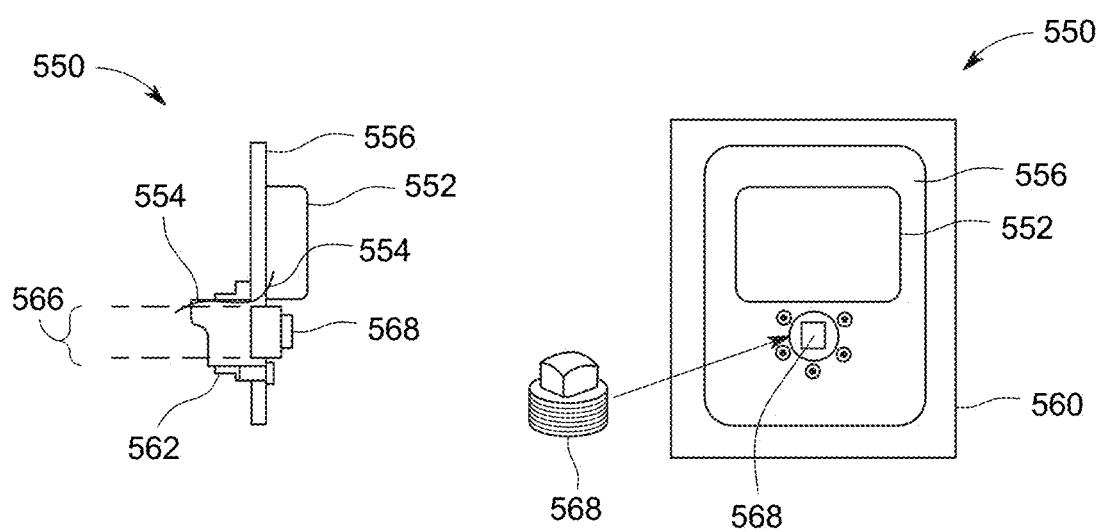
FIG. 12
FIG. 13

SYSTEM AND METHOD FOR MEASURING AN OPERATIVE CONDITION OF A MACHINE

CROSS-REFERENCE TO RELATED APPLICATIONS

This application is a continuation-in-part of U.S. patent application Ser. No. 14/421,245, filed on 12 Feb. 2015 (the "'245 application"), which is a U.S. National Phase of Patent Cooperation Treaty Application PCT/US2013/055983, filed on 21 Aug. 2013 (the "'983 application"), which claims the benefit of U.S. Provisional Patent Application No. 61/692,230, filed on 22 Aug. 2012 (the "'230 application"). The '245 application, the '983 application, and the '230 application are incorporated herein by reference in their entireties.

FIELD

One or more embodiments of the subject matter described herein relate to systems and methods for detecting an operative condition of a machine.

BACKGROUND

Some industrial machines (e.g., locomotives, trucks, earth-moving equipment, windmills, and the like) include assemblies (e.g., mechanical drive trains) that operate within environments such that they endure one or more of thermal stress, torsional stress, and shock and vibration. It may be desirable to monitor a condition of an assembly so that the assembly may be replaced or repaired before severe or permanent damage is sustained.

Sometimes, fluid lubricants may provide lubrication and cooling to increase performance of the machine and/or to increase the lifetime operation of the machine. In one example, speed control from a traction motor or other provider of mechanical power may be accomplished with a gear train or drive train. Gear trains may include at least two gears that engage each other. For instance, teeth of a first gear (e.g., pinion gear) may engage teeth of a larger gear at a gear mesh. Gears may be lubricated by a lubricant (e.g., oil) to reduce the friction between the gears and to facilitate the dissipation of heat that is generated during operation. In order for the gears to be suitably lubricated, a designated amount of lubricant is available for use by the gears.

A gear train may include a gear case that surrounds one or more parts of the gear train. The gear case has a reservoir for holding the lubricant. At least one of the gears may move through the reservoir to lubricate the gear and consequently the gear mesh. At least one of the gears may be coupled to a shaft that projects out of the gear case. To prevent leakage from the reservoir or the gear case, the interface between the shaft(s) and the gear case is sealed. In one embodiment the gear train may include a U tube coupled to the axle, and may have a reservoir for grease.

The sealed interfaces may be exposed to harsh conditions. For example, gear trains may be exposed to large differences in temperature, humid environments, dry environments, abrasive dirt or grime, and/or challenging vibratory states. These conditions may cause a failure in the sealed interface thereby resulting in leakage of the lubricant. When an insufficient supply of lubricant is available for the gears, the machine may be susceptible to gear train or rolling element bearing damage that results in a locked axle condition.

In addition to having a sufficient amount of lubricant, it may be desirable for the lubricant to have a sufficient quality during operation. For example, lubricants in a reservoir can become contaminated by water, metallic particles, and non-metallic particles. Contaminated fluids may lead to damaged parts or a decreased performance of the machine. In addition, the lubricant may age due to repetitive thermal and viscous cycles resulting in the loss of fluid properties such as viscosity.

Conventional methods of inspecting fluids of a machine include visual inspection of the fluid (e.g., dipsticks) or a sensor that is directly wired to a system. However, these methods may not be practical and/or may have limited capabilities. For example, due to the configuration of some machines, it may be difficult to visually inspect the fluid. Also, hardwired sensors may not be suitable for machines that frequently move and/or are exposed to harsh conditions.

Battery life is a concern for wireless devices that are, for example, difficult to access. Larger batteries may have longer life, but may not be suitable for applications that have space constraints. Limitations on the capabilities of various sensors have restricted their use. These limitations may include thermal resistance and current draw. Naturally, the amount of current a sensor uses may not be as relevant if power can be supplied by a wire, but in wireless systems the amount of current draw may prohibit sensors from use entirely. Additionally, the thermal capabilities for some sensors have precluded their consideration for many applications. Accordingly, existing sensing devices often, if not always, use a low temperature sensor with low power combination, particularly for wireless sensing applications. Conversely, low and high temperature sensors with high power combinations have been available for wired power applications.

It may be desirable to have a system and method for inspecting machines that differs from those that are currently available.

BRIEF DESCRIPTION

In accordance with an embodiment, a system includes a sensor operably coupled to a processor. The processor can generate one or more data signals representative of a fluid. A transmitter can wirelessly communicate the one or more data signals to a remote reader. A capacitance control structure reduces or isolates sensor capacitance from the processor.

In accordance with an embodiment, a method includes detecting a fluid level of lubricant in a gear case housing in a vehicle. In response to a detected fluid level being below a determined threshold value by un-powering an otherwise powered axle of the vehicle, where the un-powered axle is coupled with the gear case housing having the detected fluid level that is below the determined threshold, the vehicle is operated using other powered axles that are coupled to other gear case housing while the un-powered axle remains un-powered.

In accordance with an embodiment, a method includes generating, from time to time, one or more data signals from a first wireless device of a machine, the wireless device including a device body able to be coupled to the machine and a sensor configured to contact a fluid associated with the operation of the machine, and the machine being one of a fleet of machines with each machine having at least one respective wireless device. The method generates the one or more data signals from the first wireless device so that only the first wireless device is generating its one or more data signals of the at least one respective wireless devices for the machines of the fleet.

While multiple embodiments are disclosed, still other embodiments of the described subject matter will become apparent from the following description, which shows and describes illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

BRIEF DESCRIPTION OF THE DRAWINGS

FIG. 11 is a cross-section of a wireless device utilizing the sensor of FIG. 5 in accordance with an embodiment.

FIG. 12 is a cross-section of a portion of a wireless device formed in accordance with an embodiment.

FIG. 13 is a front view of the wireless device of FIG. 13.

DETAILED DESCRIPTION

Figure 1:
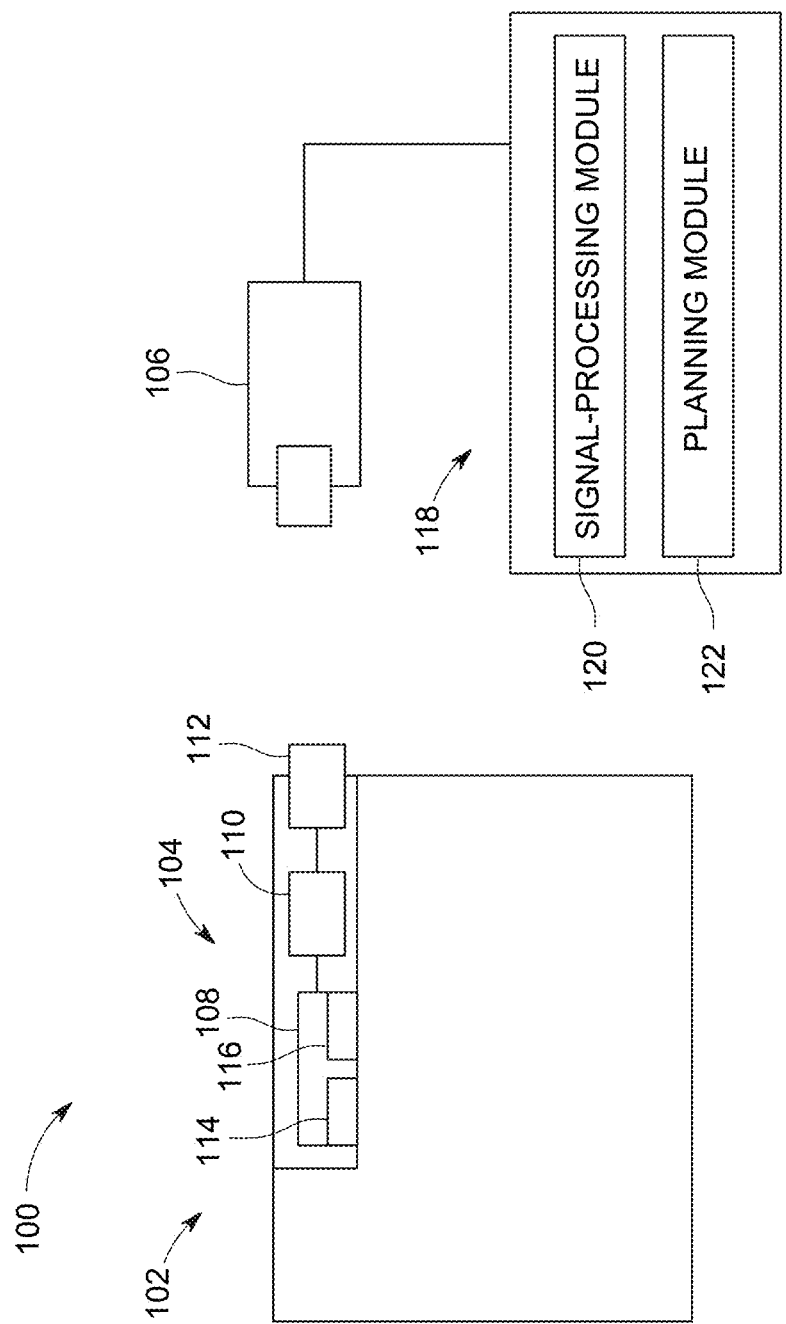
FIG. 1 is a schematic view of a system in accordance with an embodiment.

One or more embodiments of the subject matter described herein relate to systems and methods for detecting an operative condition of a machine. Embodiments described herein include various systems, assemblies, devices, apparatuses, and methods that may be used in a connection with obtaining one or more measurements of a machine. The measurement(s) may be representative or indicative of an operative condition of the machine.

As used herein, an "operative condition of the machine" may refer to an operative condition of the machine as a whole or an operative condition of a component (e.g., element, assembly, or sub-system) of the machine. The term "operative condition" relates to a present state or ability of the component and/or a future state or ability. For example, the measurement may indicate that a component is not functioning in a sufficient manner, is damaged, is likely to be damaged if it continues to operate in a designated manner, is not likely to perform appropriately under designated circumstances, and/or is likely to cause damage to other components of the machine.

As an example with respect to vehicles, one or more measurements obtained from a vehicle may indicate that a lubricant in the component (e.g., drive train, gearbox, engine, and the like) is low or has an insufficient quality. Embodiments set forth herein may generate an operating plan that is based on the measurement(s). For instance, the operating plan may include instructions to disable an axle or to limit tractive and/or braking efforts of the axle. The operating plan may indicate which element of the gearbox should be replaced and/or how the machine is to be operated until the gearbox is replaced. Such operating plans are described in greater detail below.

The measurement may be one of a plurality of measurements that are analyzed according to embodiments described herein. For instance, embodiments may comprise analyzing multiple measurements that were obtained at different times from a single sensor to determine an operative condition of the machine. By way of example, a series of measurements from a single sensor in a gear case may indicate that a lubricant level has substantially changed and, thus, the gear case is leaking. Embodiments may include analyzing measurements from a plurality of sensors of the same type. For example, machines may include multiple gearboxes. Vibration measurements from the gearboxes may indicate that one of the gearboxes is operating differently than the others and, thus, may be damaged or in need of maintenance. Embodiments may include analyzing different types of measurements to determine an operative condition of the machine. For example, the vibration measurements may be analyzed in light of the speed at which the gears are driven and/or current environmental conditions. Additional measurements or factors are set forth below.

The measurements may be wirelessly transmitted from a device to a reader, which may be referred to as a receiver. For example, radio waves representative of the measurement(s) may be transmitted from a transmitter (e.g., antenna) of the wireless device to a remote reader. The reader may be a handheld reader (e.g., capable of being carried in a single hand by a technician) or an otherwise movable reader. In some embodiments, the reader may have a fixed position. For example, for embodiments in which the machine is a vehicle, the reader may have a stationary position along a designated path that is traversed by the vehicle (e.g., railroad tracks, weighing stations, tollbooths). When a vehicle passes the reader, the reader may interrogate one or more wireless devices to obtain measurements. Remote readers may also be located on-board the vehicle. For example, a vehicle may have a control system that receives data from multiple sources, including one or more wireless devices that communicate the measurements to the control system.

The measurement may be detected or obtained by a sensor when the device having the sensor is interrogated by the reader. Alternatively or additionally, the sensor may obtain data at designated intervals (e.g., one measurement/hour, one measurement/minute, and the like) and/or when a designated event occurs. For example, measurements may only be obtained after the vehicle has been interrogated or after the vehicle has remained stationary for a certain amount of time (e.g., ten minutes). In some embodiments, the wireless device includes a storage unit (e.g., memory) where multiple measurements may be stored or logged. The wireless devices may include a power source that is integral to the device. Examples of electrical power sources include batteries and energy harvesting devices. Energy harvesting devices convert energy in the surrounding environment, such as kinetic energy (e.g., vibrations), thermal energy, and electromagnetic energy. In particular embodiments, the wireless devices may include or be coupled to a vibratory energy harvesting device that converts kinetic energy into electrical energy.

The foregoing description of certain embodiments of the inventive subject matter may be understood when read in conjunction with the appended drawings. To the extent that the figures illustrate diagrams of the functional blocks of various embodiments, the functional blocks are not necessarily indicative of the division between hardware and circuit. Thus, for example, one or more of the functional blocks (for example, controllers or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

FIG. 1 is a schematic diagram of a system 100 formed in accordance with one embodiment. The system may obtain one or more measurements that are representative of an operative condition of a machine 102. The machine may include one or more components, elements, assemblies, or sub-systems. The machine may be motive or may be non-motive. Suitable motive machines or vehicles may include on-road vehicles and off-highway vehicles (e.g., vehicles that are not designed or allowed by law or regulation to travel on public roads, highways, and the like). Off-highway vehicles include locomotives, mining vehicles, construction equipment, agricultural equipment, industrial equipment, marine vessels, and the like. In some cases, the vehicle may be part of a vehicle consist in which multiple vehicles are linked directly or indirectly to one another in a common vehicle system (e.g., a train or a platoon of trucks). In some embodiments, the machine may be an automobile or truck. A suitable non-motive machine may be, for example, a wind turbine or a power-generating turbine.

The operative condition may relate to a health or status of a designated component of the machine. Non-limiting examples of such components include a gearbox, a gear case, a U-tube, an air compressor, a turbo-charger, or a drive train. The measurement may be analyzed to determine, for example, that a component is damaged, is operating improperly (e.g., insufficiently or not at all), and/or is operating in a manner that will lead to or cause greater damage to the component or other component of the machine.

In particular embodiments, the operative condition may be determined based on an amount and/or a quality of liquid used by the machine and/or a vibratory state of the machine. For instance, in some embodiments, the component may be a gear case that has a reservoir for storing a lubricant liquid. A low level or quantity of the liquid in the reservoir may indicate that the gear case is damaged. In particular, a low level or quantity may indicate that the gear case is leaking the liquid. In other embodiments, a component may have a particular vibratory state(s) when the component is operating properly. For example, a mechanical element may oscillate in a known or expected manner during operation. However, if the mechanical element is damaged or operating improperly, the mechanical element may have a different vibratory state.

As shown, the system may include a wireless device 104 that can wirelessly communicate data signals to a remote reader 106. The data signals may represent the measurement(s) obtained by the wireless device 104. To this end, the wireless device may include a sensor 108, a processing unit 110, and a transmitter 112. The sensor is configured to measure an operating parameter of the machine and thereby obtain a measurement. In some embodiments, the sensor includes a detector or transducer 114 and an activator 116. The activator may provide a stimulus (e.g., sound waves, light, electric current, etc.) that causes a response by a component-of-interest or is affected by the component-of-interest. The detector may detect the response that is caused by the stimulus or the affect that the component-of-interest has on the stimulus. For example, the stimulus may be sound waves that are detected to determine a liquid level (e.g., sonar). The stimulus may be light signals that are projected by a laser into a liquid to determine how much of the light signals are absorbed by the liquid. Another stimulus may be electric current. In other embodiments, the sensor does not include the activator. Instead, the detector may detect sound, vibrations, light, temperature, electrical properties, or other properties that occur in the environment without a stimulus provided by an activator.

The processing unit is operably coupled to the sensor. The processing unit is configured to receive measurement signals from the sensor and process the measurement signals to provide data signals. The processing unit may be an analog-to-digital converter (ADC). Alternatively or in addition to the ADC, the processing unit may include a logic-based device that transforms the measurement signals into data signals. The data signals may then be configured to be transmitted to the reader by the transmitter. For example, the processing unit may be a computer processor, controller (e.g., microcontroller) or other logic-based device that performs operations based on one or more sets of instructions (e.g., software). The instructions on which the processing unit operates may be stored on a tangible and non-transitory (e.g., not a transient signal) computer readable storage medium, such as a memory. The memory may include one or more types of memory, such as hard drives, flash drives, RAM, ROM, EEPROM, and the like. Alternatively, one or more of the sets of instructions that direct operations of the processing unit may be hard-wired into the logic of the processing unit, such as by being hard-wired logic formed in the hardware of the processing unit.

The transmitter may be coupled to the processing unit and can wirelessly communicate the data signals to the reader. In some embodiments, the transmitter is a transceiver, which transmits the data signals and receives other signals. These other signals may include interrogation signals from the reader.

In some embodiments, the sensor, the processing unit, and the transmitter are localized within and/or attached directly to the machine such that the sensor, the processing unit, and the transmitter are proximate to each other and form a single device. The sensor, the processing unit, and the transmitter may be in a localized spatial region of the machine that is separate from a computing system that controls operation of the machine. For example, the processing unit and the transmitter may be integrated with the same component such that the processing unit and the transmitter have fixed positions with each other. The processing unit and the transmitter may be at least partially integrated onto a common container (e.g., circuit board) and/or positioned within a common container or housing that is coupled to the machine. The common container may not be coextensive with the machine and, instead, may be a separate component that is attached to or disposed within the machine-of-interest. By way of example only, some or all of the components of the processing unit and the transmitter may be located less than 50 centimeters (cm) from each other. In various embodiments, depending on the types of components selected and the relevant application, the components may be less than 20 cm of each other, 10 cm of each other or, within 5 cm of each other.

In some embodiments, the processing unit and the transmitter may be part of a common radio frequency identification (RFID) unit (e.g., tag, chip, card, and the like). Optionally, the sensor may also be part of the common RFID unit. In other cases, the sensor is separate from, but operably coupled to, the RFID unit and is only a short distance from the RFID unit. For example, the sensor may be located within 50 cm of the RFID unit and communicatively coupled via wires or wireless communication. The RFID unit may be formed in accordance with RFID technology, which may include integrated circuit technology. For example, the RFID unit may be an electronic circuit that is capable of wireless communication. In some instances, the RFID unit may satisfy one or more established RFID standards and/or guidelines, such as standards and guidelines formed by the International Organization for Standardization (ISO), the International Electrotechnical Commission (IEC), ASTM International, the DASH7 Alliance, EPCglobal, the Financial Services Technology Consortium (FSTC) (all of which are incorporated herein by reference).

In certain embodiments, the wireless device is not physically and electrically connected (e.g., not connected by wires or other conductors) to any of the one or more computers or other controller-based units in the machine. For example, in the context of trains, the wireless device may be partially disposed within a reservoir and/or attached to a wall that defines the reservoir and is not physically electrically connected to the computing system that controls operation of the train. In such embodiments, the data signals from the wireless device may be wirelessly transmitted from the wireless device to, for example, a reader that is on-board or off-board. More specifically, the data signals may not be transmitted via wire/cables or other physical electrical connections. In one or more embodiments, at least portions of the processing unit and the transmitter may be directly connected to a wall that defines the reservoir (e.g., a wall that bears a pressure of and/or contacts the liquid in the reservoir) and/or to a structure immediately connected to the wall (e.g., support structure of the reservoir, gear case, or the like).

Various forms of wireless communication may be transmitted and received by the wireless device. For example, the transmitter may receive and/or transmit radio signals, optical signals, signals based on sound, or signals based on magnetic or electric fields. In particular embodiments, the transmitter is configured to receive and/or transmit radio signals in one or more radio frequencies. The wireless signals may be transmitted along a narrow radio band. In narrow band transmission, a single carrier frequency is used. Alternatively, the wireless signals may be transmitted within a spectrum of radio frequencies. For example, in spread spectrum transmission, the signals may be transmitted over a number of different radio frequencies within a radio band. The data signals may be modulated for transmission in accordance with any one of a number of modulation standards, such as frequency-hopping spread spectrum (FHSS), direct-sequence spread spectrum (DSSS), or chirp spread spectrum (CSS).

One wireless communication standard that may be used by embodiments described herein is IEEE 802.15.4 (incorporated by reference). The IEEE 802.15.4 standard may operate within one of three frequency bands: (1) 868.0-868.6 MHz; (2) 902-928 MHz; or (3) 2400-2483.5 MHz. A number of channels may be used in each of the frequency bands. Embodiments may also use frequency bands that are associated with RFID technology, such as 120-150 kHz, 13.56 MHz, 865-868 MHz, 902-028 MHz, 2450-5800 MHz, or 3.1-10 GHz. Ultra wideband (UWB) may also be used. In some embodiments, a transmission range of the data signals and/or the signals from the reader is in a range of from about 1 centimeter to about 20 meters. In other embodiments, the transmission range may be greater, such as up to 100 meters or more.

Various embodiments may be based on or consistent with RFID technology. For example, the wireless device may be a passive sensor, a semi-passive sensor, or an active sensor. A passive sensor may not include a power source. Instead, the power may be based on inductive coupling or backscatter coupling with the reader. A semi-passive sensor may include a power source for only designated functions. For example, a battery and/or an energy harvesting device may be used to increase the transmission distance. The passive and semi-passive sensors may be particularly suitable for when the reader is present (e.g., within transmission range so that the sensors can be powered by the reader). An active sensor may include a power source for powering multiple functions (e.g., detection, reception, and transmission). Active sensors may be used in embodiments in which the reader can only receive data signals and not transmit interrogation signals.

The reader may be operably connected to a control system 118 having a signal-processing or diagnostic module 120 and, optionally, a planning module 122. Like the processing unit, the modules may be a computer processor, controller (e.g., microcontroller), or other logic-based device that performs operations based on one or more sets of instructions. The instructions on which the modules operates may be stored on a tangible and non-transitory (e.g., not a transient signal) computer readable storage medium, such as a memory. Alternatively, one or more of the sets of instructions that direct operations of the modules may be hard-wired into the logic of the modules. The module may be located on separate devices (e.g., separate processors) or may be located on common processor.

The signal-processing module may determine, based on the data signals received by the reader, whether the machine is operating improperly. The signal-processing module may determine whether the machine is operating properly or improperly by analyzing the data signals that are representative of the measurements. For example, the signal-processing module may use a look-up table or other databases that provides acceptable ranges of operation. If the measurement based on the data signals is not within the range, the signal-processing module may determine that the machine is not operating properly. In some cases, based on the measurement(s), the signal-processing module may be able to determine whether a particular component of the machine is in need of maintenance, repair, or replacement or whether the machine requires an overhaul of a sub-system.

Based on the measurement(s), the signal-processing module may request that an operating plan be generated by the planning module. The operating plan may improve the performance of the machine and/or to limit the performance of the machine to prevent damage or additional damage. The operating plan may include instructions for replacing, maintaining, modifying, and/or repairing a designated component or components of the machine.

The operating plan may be based on the operative condition, which is at least partially a function of the measurement(s) obtained. For instance, if a capacitive measurement indicates that the liquid level is less than sufficient, but a substantial amount remains in the gear case, then the operating plan may include instructions for refilling the liquid at a first facility and then resealing the gear case at a second facility located further away. However, if a capacitive measurement indicates that the liquid level quickly reduced to little or no measurable amount of liquid, then the operating plan may instruct that the gear case be replaced at a designated facility.

In the context of a locomotive or other vehicle, the operating plan may include instructions for controlling tractive and/or braking efforts of the vehicle. In particular, the operating plan may be partially based on the measurements of the operative condition of the machine. The instructions may be expressed as a function of time and/or distance of a trip along a route. In some embodiments, travel according to the instructions of the operating plan may cause the vehicle to reduce a stress on a component-of-interest of the machine than the component would typically sustain during normal operation. For example, the operating plan may instruct the vehicle to reduce horsepower delivered to an axle, to intermittently drive the axle, or to disable the axle altogether. The vehicle may be autonomously controlled according to the operating plan or the instructions of the operating plan may be presented to an operator of the vehicle so that the operator can manually control the vehicle according to the operating plan (referred to as a vehicle "coaching mode").

In some embodiments, the operating plan that is generated when it is determined that the machine is operating improperly is a "revised" operating plan that supersedes or replaces another operating plan. More specifically, due to the newly acquired measurements, the control system may determine that the currently-implemented operating plan should be modified and, as such, may generate a revised operating plan to replace the other.

Operating plans may be optimized to achieve designated goals or parameters. As used herein, the term "optimize" (and forms thereof) are not intended to require maximizing or minimizing a characteristic, parameter, or other object in all embodiments described herein. Instead, "optimize" and its forms may include increasing or decreasing (as appropriate) a characteristic, parameter, or other object toward a designated or desired amount while also satisfying other conditions. For example, optimized stress levels on a component may not be limited to a complete absence of stress or that the absolute minimum amount of stress. Rather, optimizing the stress level may mean that the stress is controlled, while also satisfying other conditions (e.g., speed limits, trip duration, arrival time). For example, the stress sustained by a component may be controlled so that the vehicle may arrive at its destination without the component being severely damaged.

The planning module may use at least one of vehicle data, route data (or a route database), part data, or trip data to generate the operating plan. The vehicle data may include information on the characteristics of the vehicle. For example, when the vehicle system is a rail vehicle, the vehicle data may include a number of rail cars, number of locomotives, information relating to an individual locomotive or a consist of locomotives (e.g., model or type of locomotive, weight, power description, performance of locomotive traction transmission, consumption of engine fuel as a function of output power (or fuel efficiency), cooling characteristics), load of a rail vehicle with effective drag coefficients, vehicle-handling rules (e.g., tractive effort ramp rates, maximum braking effort ramp rates), content of rail cars, lower and/or upper limits on power (throttle) settings, etc.

Route data may include information on the route, such as information relating to the geography or topography of various segments along the route (e.g., effective track grade and curvature), speed limits for designated segments of a route, maximum cumulative and/or instantaneous emissions for a designated segment of the route, locations of intersections (e.g., railroad crossings), locations of certain track features (e.g., crests, sags, curves, and super-elevations), locations of mileposts, and locations of grade changes, sidings, depot yards, and fuel stations. The route data, where appropriate, may be a function of distance or correspond to a designated distance of the route.

Part data may include, for example, historical data or proprietary data regarding the lifetime operability of a component. The data may include baseline data for a designated speed and/or load on the machine. Additional factors may be part of the baseline data. For example, if the lubricant has a designated quantity in the gear case, the part data may include data from identical components that operated with an approximately equal lubricant level. The data may include how long the component is capable of operating at a designated speed.

Trip data may include information relating to a designated mission or trip, such as start and end times of the trip, start and end locations, route data that pertains to the designated route (e.g., effective track grade and curvature as function of milepost, speed limits), upper cumulative and/or instantaneous limits on emissions for the trip, fuel consumption permitted for the trip, historical trip data (e.g., how much fuel was used in a previous trip along the designated route), desired trip time or duration, crew (user and/or operator) identification, crew shift expiration time, lower and/or upper limits on power (throttle) settings for designated segments, and the like. In one embodiment, the planning module includes a software application or system such as the Trip Optimizer™ system developed by General Electric Company.

Figure 2:
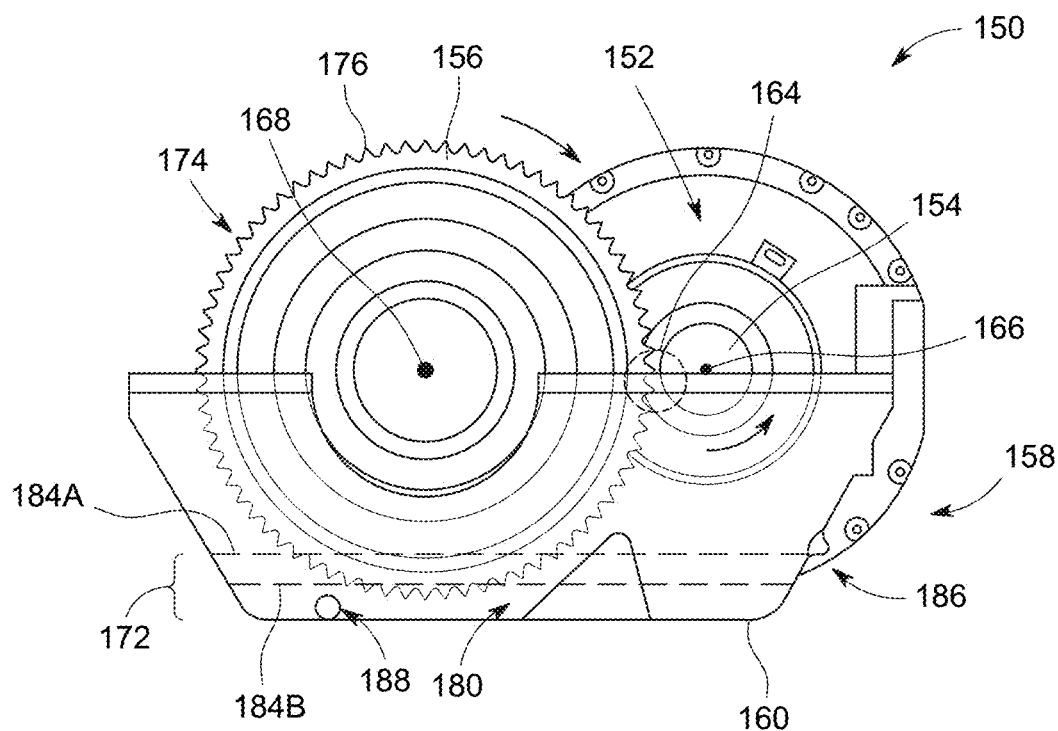
FIG. 2 is a side view of a drive train in accordance with an embodiment.
Figure 3:
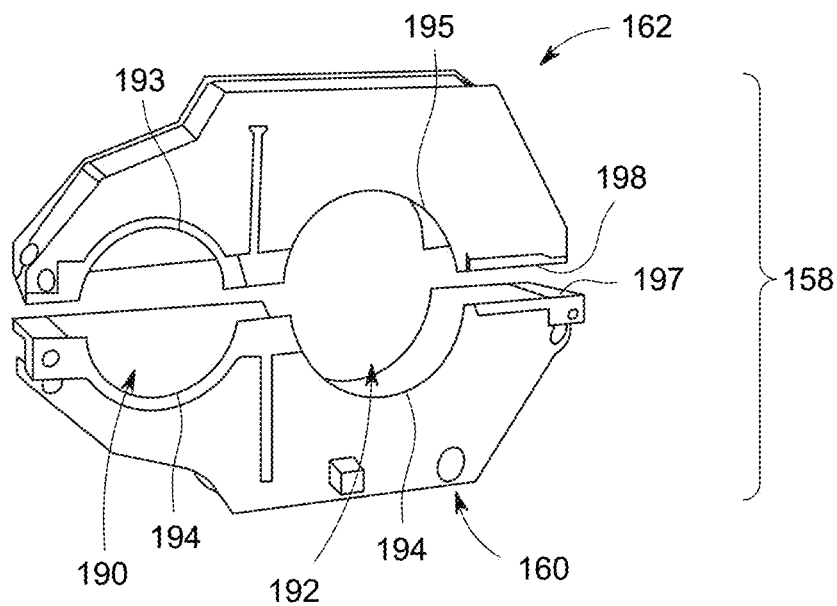
FIG. 3 is a partially exploded view of a gear case that may be used by the drive train of FIG. 2.

FIG. 2 is a side view of a drive train (or final drive) 150 in accordance with one embodiment. The drive train includes a traction motor 152, a first (or pinion) gear 154, a second gear 156, and a base portion or shell 160 of a gear case 158. A top portion or shell 162 of the gear case is shown in FIG. 3. As shown in FIG. 2, the first gear and the second gear engage each other at a gear mesh 164. During operation of the drive train the traction motor drives the first gear by rotating an axle (not shown) coupled to the first gear about an axis of rotation 166. The first gear may be rotated, for example, in a counter-clockwise direction as viewed in FIG. 2. Due to the engagement at the gear mesh 164, the first gear rotates the second gear in a clockwise direction about an axis of rotation 168. The second gear is coupled to an axle (not shown) that rotates with the second gear. The axle of the second gear is coupled to wheels (not shown) that are rotated with the axle. The wheels engage a surface (e.g., rails or tracks) to move the machine.

The gear case includes a reservoir 172 that holds a lubricant liquid 180 (e.g., oil). The gear case has a fill or inlet port 186 and a drain or outlet port 188. The liquid may be provided to the reservoir through the fill port and drained through the drain port.

As shown in FIG. 2, the second gear has teeth 176 along an edge 174 of the second gear. When the liquid is held within the gear case, the liquid may have a fill level 184. FIG. 2 illustrates a first fill level 184A and a second fill level 184B. The second fill level is lower than the first fill level. In some embodiments, when the drive train is operating properly, the quantity of the liquid correlates to the first fill level such that the edge of the second gear is sufficiently submerged within or bathed by the liquid. However, when the fill level is lowered to, for example, the fill level, the edge and teeth may be insufficiently lubricated. Such circumstances may occur when the gear case has a leak.

FIG. 3 is a partially exploded view of the gear case and illustrates the base and top portions before the base and top portions are coupled to the drive train to surround the first and second gears. As shown, the gear case may include first and second gear-receiving openings 190, 192 that are sized to receive the first and second gears (FIG. 2), respectively. The gear-receiving openings may be defined by opening edges 193-196 and the base and top portions may engage each other along case edges 197, 198.

When the drive train is fully constructed and operational, the opening edges engage the portions of the drive train along sealable interfaces. The case edges may couple to each other along a sealable interface. During operation of the drive train, however, the interfaces may become damaged or worn such that the interfaces are no longer sufficiently sealed. For example, when the drive train is part of a locomotive, the opening edges or the case edges may become worn, damaged, or separated such that the liquid is permitted to escape the reservoir. Accordingly, the amount of liquid may reduce such that the fill level lowers.

Embodiments described herein may detect that the amount of liquid has reduced. In addition, due to the wear, damage, or separation of the base and top portions, the gear case (or portions thereof) may exhibit different vibratory characteristics. For example, a gear case that is sufficiently sealed with respect to the drive train and has a sufficient fill level may exhibit a first vibratory state when the drive train is driven at a first speed. However, a gear case that is insufficiently sealed with respect to the drive train and/or has an insufficient fill level may exhibit a second vibratory state that is different than the first vibratory state when the drive train is driven at the first speed. Embodiments described herein may detect and measure the different vibratory states. In certain embodiments, a wireless device, such as those described herein, is at least partially disposed within the reservoir and/or directly attached to a portion of the gear case. For example, at least a portion of the wireless device may be directly secured or affixed to a wall of the gear case, such as the wall that defines the reservoir. In some embodiments, the wireless device is not physically and electrically connected to other components of the machine, such as a computing system that controls operation of the machine.

In addition to liquid level and vibrations, embodiments may detect other characteristics. For example, other measurements may relate to a quality (e.g., degree of contamination) of the liquid. Contaminants may include water, metallic particles, and/or non-metallic particles. Furthermore, embodiments are not limited to the drive train or a gear case of the drive train. For example, measurements that may be obtained for a drive train may also be obtained for a turbo-charger, an air compressor, an engine, and the like. Other components of a machine may also be measured by wireless devices described herein.

Figure 4:
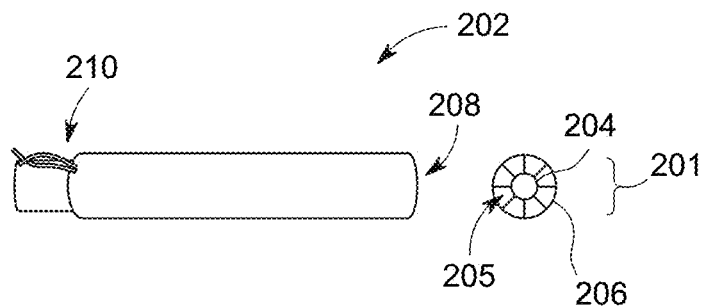
FIG. 4 is a side view of a capacitive-type sensor in accordance with an embodiment.
Figure 5:
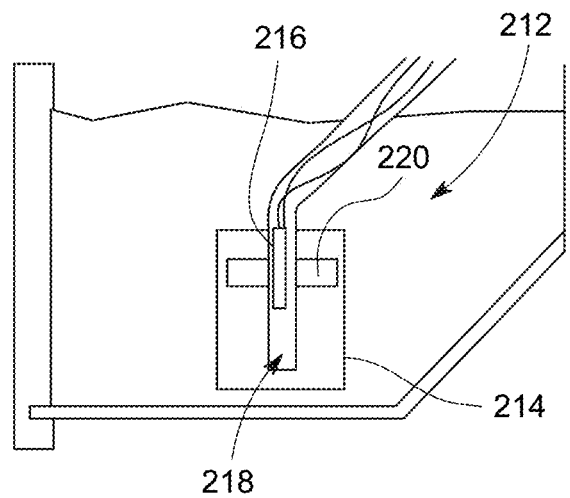
FIG. 5 is a schematic view of a magnetic float/reed switch sensor in accordance with an embodiment.
Figure 6:
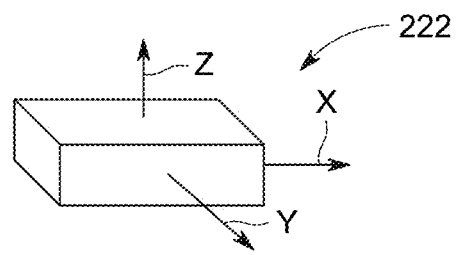
FIG. 6 is a schematic view of an accelerometer in accordance with an embodiment.

FIGS. 4-6 illustrate sensors 202, 212, 222, respectively. The sensors, which may be transducers in some embodiments, may be a portion of some wireless devices described herein. Each of the sensors may measure (e.g., detect) a designated property or characteristic in the environment proximate to the sensor and provide a signal that is representative of the measured property or characteristic. The signal provided by the sensor may be the measurement.

Various types of measurements may be obtained by the sensors. Some non-limiting examples include a capacitance of a liquid, a temperature of a liquid and/or temperatures of certain parts of a machine, a fluid conduction of a liquid, a dielectric constant of a liquid, a dissipation factor of a liquid, an impedance of a liquid, a viscosity of a liquid, or vibrations of a mechanical element. A measurement may be directly obtained (e.g., temperature) by the sensor, or a designated measurement may be obtained after using information provided by the sensor to calculate the designated measurement. For example, the viscosity of the liquid may be calculated based on multiple level measurements obtained by a sensor.

Embodiments may include a single wireless device that measures and communicates only a single measurement (e.g., capacitance) or multiple measurements (e.g., inductance (L), capacitance (C), and resistance (R) or "LCR"). In one embodiment, a single wireless device may measure and communicate multiple types of measurements (e.g., capacitance of the liquid, temperature of the liquid, temperature of the sensor, shock and/or vibration of the gear case, and the like). In one embodiment, the wireless device may have multiple sensors and these may be of multiple types.

In the illustrated embodiment, the sensor may measure a capacitance of a liquid, such as a lubricant in a tank (e.g., gear case). Such a sensor may be referred to as a capacitive level probe. For reference, a cross-section 201 of the level probe is shown in FIG. 4. The level probe extends lengthwise between a leading end 208 and a trailing end 210. The level probe includes an inner or measurement electrode 204 and an outer or reference electrode 206. As shown, a space 205 exists between the inner and outer electrodes. A capacitance of the material that exists within the space may be measured by the level probe. The material may be one of, or a combination of, a liquid and a gas. Other suitable materials may include liquids and/or gases that include suspended solids or dissolved materials. Suitable liquids may include polar liquids (e.g., water), non-polar liquids (e.g., oil), or combinations thereof (e.g., emulsions). In some embodiments, a wall of the tank that holds the liquid may be used as the reference electrode.

The level probe may be immersed into the liquid held by the tank. For example, the leading end may be inserted into the liquid. As the leading end is submerged, the liquid may flow into the space thereby changing a ratio of liquid to gas within the space. As such, the measured capacitance may change as the level of the liquid within the space changes. If the liquid is a lubricant, the measured value of capacitance decreases as an amount or level of the liquid decreases. As an amount or level of the liquid increases, the measured value of capacitance may increase.

The level probe may determine a quality of the liquid. More specifically, the level probe may detect an amount or percentage of contaminations in the liquid based on capacitance measurements. For example, contaminant detection may be based on a dissipation factor of a dielectric of the liquid. In general, the dissipation factor is a function of an applied frequency, a liquid temperature, a composition of the liquid (e.g., the desired composition of the liquid), and contaminants. The dissipation factor may be substantially independent of the base capacitance or liquid level.

In some cases, movement of the machine may cause a displacement of the liquid which may introduce an error in the measurements. Accordingly, in some embodiments, the level probe is only activated when the machine or component thereof is at rest (e.g., inactive). To this end, an accelerometer or other inertial type sensor may be part of or operably coupled to the wireless device that includes the level probe. The accelerometer may determine that the machine is in an inactive or stationary state such that measurements may be obtained by the level probe.

As shown in FIG. 5, the sensor includes a body float 214 and a reed switch 216. The body float includes a cavity 218 that is sized and shaped to receive the reed switch. The body float floats along the reed switch (e.g., vertically) based on a level of the liquid in the reservoir. The body float includes a permanent magnet 220, and the reed switch includes a magnetically actuated switch or switches (not shown). As the body float moves up and down, the permanent magnet may activate or deactivate the switch (e.g., close or open a circuit, respectively, in the reed switch). The activated switch indicates that the body float is at a designated level and, consequently, that the liquid is at a designated level.

As described above, one or more embodiments may include a sensor system that includes an accelerometer. FIG. 6 illustrates one such sensor system, which is referenced as an accelerometer 222. A suitable accelerometer may be a micro-electro-mechanical system (MEMS) tri-axis accelerometer. The accelerometer may be used for a variety of functions, from movement to impact to vibration. For example, the accelerometer may be coupled to a mechanical element, such as a tank to determine whether the mechanical element has remained stationary for a designated amount of time. In some embodiments, other measurements (e.g. liquid level) may be obtained in response to an external trigger, such as a determination that the mechanical element has remained stationary for the designated amount of time.

Alternatively or additionally, the accelerometer may detect vibratory states experienced by the mechanical element. For example, the accelerometer may obtain numerous shock and vibrations measurements per second in each of x-, y-, and z-axes. For example, the accelerometer may be able to log hundreds or thousands of data points per second in each of the x-, y-, and z-axes.

Figure 7:
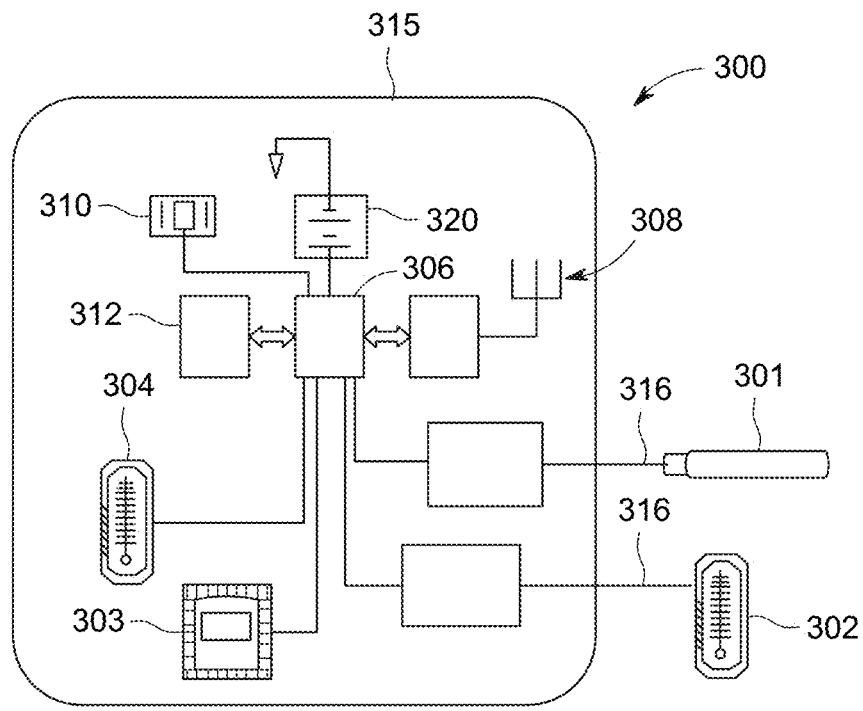
FIG. 7 is a schematic diagram of a wireless device formed in accordance with an embodiment.

FIG. 7 is a schematic diagram of a wireless device 300 formed in accordance with one embodiment. The wireless device includes sensors 301-304, a processing unit 306 (e.g., microprocessor), a transmitter 308, an internal clock 310 (e.g., real-time clock crystal), and a memory 312 (e.g., non-volatile memory). The wireless device has a device body 315, which may include a printed circuit board (PCB) or a die (e.g., semiconductor wafer) in some embodiments. In the illustrated embodiment, the device body includes the sensors, the processing unit, the transmitter, the internal clock, and the memory. In alternative embodiments, however, the wireless device may have multiple bodies (e.g., multiple dies) that are coupled to each other and/or the components described herein may be separate from the device body. The sensors may be operably coupled to the device body through, for example, wires 316. In other embodiments, the sensors may be wirelessly coupled to the device body.

A suitable sensor may be a level probe, such as the level probe described with respect to FIG. 4. The sensor may be inserted into a liquid (e.g., lubricant) of a machine. The sensor may be a thermometer that can obtain a temperature of the liquid. The sensor may be an accelerometer, or may be another thermometer that can determine a temperature of the device body of the wireless device. Each of the sensors 301-304 may be communicatively coupled to the processing unit and can communicate signals to the processing unit. The signals may be representative of a property or characteristic detected by the sensor.

The processing unit may store or log data (e.g., data based on the signals obtained from the sensors) in the memory. In some embodiments, the processing unit may query the sensors and thereby request measurements from the sensors. The queries may occur at determined times or in response to an occurrence of a designated event. For example, the queries may occur once an hour as determined by the internal clock until, for example, the wireless device is interrogated by a reader (not shown). At such an event, the processing unit may query the sensors for numerous data points. For example, the data points may be provided almost continuously after interrogation. The processing unit may receive data from the memory. The data received from the sensors and/or the memory may be transformed into data signals that are communicated by the transmitter to the reader.

The wireless device 300 may be characterized as an active or semi-passive device. For example, the wireless device 300 may include a power source 320, such as a battery (e.g., lithium thionyl chloride battery) and/or kinetic energy harvesting device. The wireless device 300 may utilize the power source 320 to increase the transmission range of the transmitter 308. In such embodiments, the reader may be located tens or hundreds of meters away from the wireless device 300. In addition to the transmitter 308, the power source 320 may be used to supply power to other components of the wireless device 300, such as the sensors 301-304 or the processing unit 306.

Figure 8:
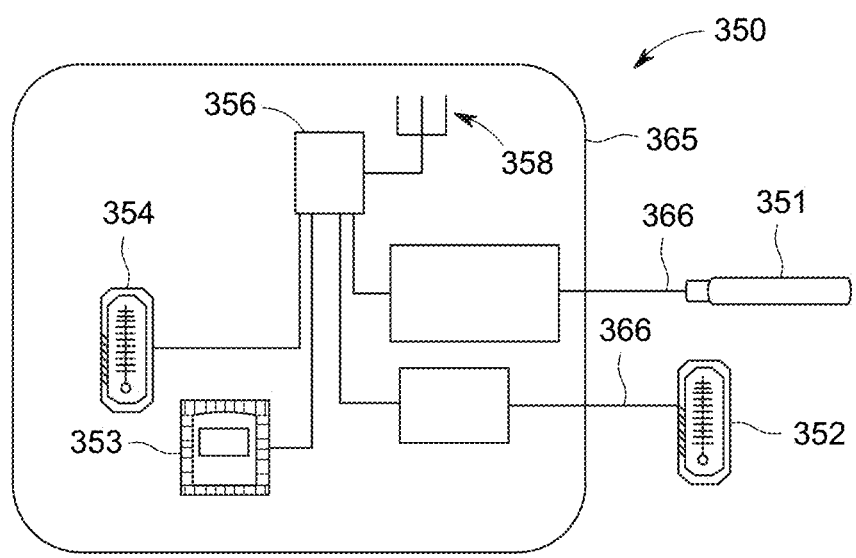
FIG. 8 is a schematic diagram of a wireless device formed in accordance with an embodiment.

FIG. 8 is a schematic diagram of a wireless device 350 formed in accordance with one embodiment. The wireless device 350 may be a passive device such that the wireless device 350 is powered by inductive or backscatter coupling with the reader (or some other non-internal power source). As shown, the wireless device 350 includes sensors 351-354, a processing unit 356, and a transmitter 358. The wireless device 300 has a device body 365 that includes, in the illustrated embodiment, the sensors 353, 354, the processing unit 356, and the transmitter 358. The device body 365 may be formed by integrated circuit technology. For example, the device body 365 may include one or more printed circuit boards (PCBs). The sensors 351 and 352 may be operably coupled to the device body 365 through, for example, wires 366. Similar to the wireless device 300 (FIG. 7), the sensors 351-354 may be a level probe, external thermometer, an accelerometer, and an internal thermometer, respectively.

In some embodiments, the processing unit executes fewer calculations or conversions of the signals from the sensors 351-354 than the processing unit (FIG. 7). For example, the processing unit may be an ADC that converts the analog signals from the sensors 351-35 to digital signals. The digital signals may be the data signals that are then transmitted by the transmitter. In the illustrated embodiment, the processing unit may only query the sensors after being interrogated by a reader (not shown). More specifically, the interrogation signals from the reader may power the processing unit to query the sensors and transmit the data signals.

Figure 9:
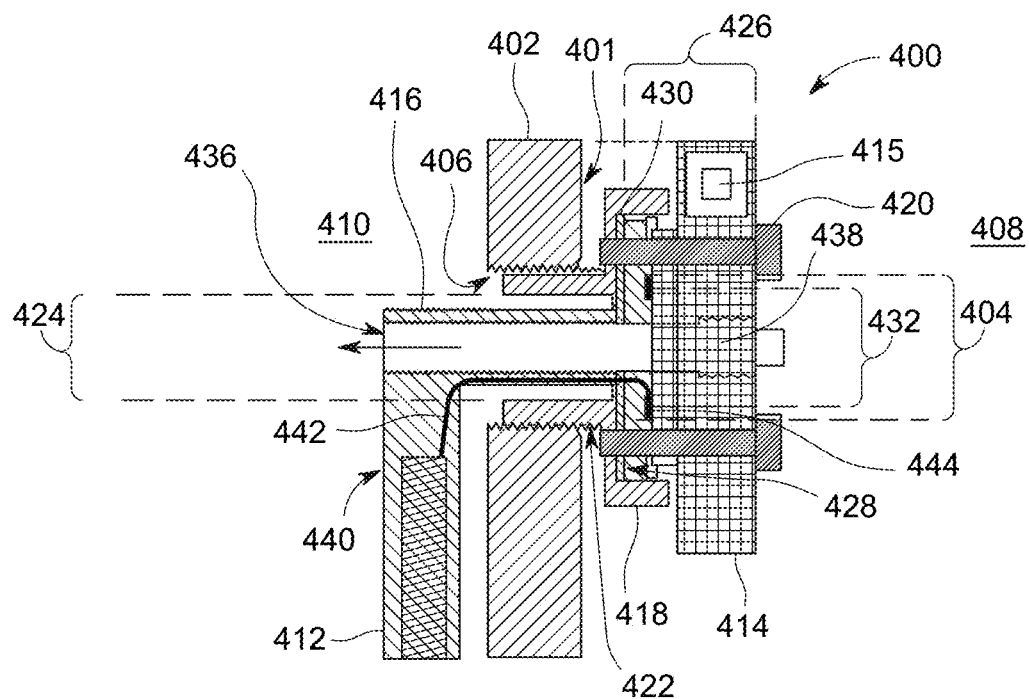
FIG. 9 is a cross-section of a portion of a wireless device utilizing the sensor of FIG. 4 in accordance with an embodiment.

FIG. 9 is a cross-section of a portion of a wireless device 400 attached to a wall 402 of a tank 401 that may be secured to a machine. Depending on the type and purpose of the tank, different fluids may be contained within. Suitable fluids may include lubricant, fuel, coolant, exhaust gases, and the like. A fill port 404 in the wall is defined by interior threads 406 of the wall as shown in FIG. 9. The fill port may provide access from an exterior 408 of the tank to a reservoir 410, which may be used for holding the fluid.

As shown, the wireless device includes a sensor 412, a device body 414, and an intermediate cable portion 416 that joins the sensor and the device body. The wireless device may include a coupling component 418 that may be secured to the device body 414 through one or more fasteners 420 and attached to the wall. In the illustrated embodiment, the coupling component includes complimentary threads 422 that complement and rotatably engage the threads of the wall. In other embodiments, suitable methods of attaching the coupling component to the tank may be used, such as latches, interference fits (e.g., plugs), and/or adhesives.

To assemble the wireless device, the coupling component may be rotatably engaged to the wall. The sensor and the cable portion may be inserted through an opening 424 of the coupling component and the fill port. As shown, the coupling component has a mating face 428 that faces in a direction away from the wall. The cable portion has a mating end 426 that is located in the exterior of the tank and may be pressed toward the mating face with a gasket 430 located therebetween. The device body has a cable opening 432 that receives an end of the cable portion. The device body may be secured to the cable portion and the coupling component using the fasteners. As shown, the cable portion includes a fill channel 436 that permits access to the reservoir. During operation, the fill channel may be closed with a plug 438 at the mating end of the cable portion.

The sensor may be the same as the level probe described in FIG. 4. A trailing end 440 of the sensor may be as shown in FIG. 9. The trailing end is coupled to wires 442 that communicatively couple the sensor to the device body. In other embodiments, the sensor 462 may be similar or identical to the sensor shown in FIG. 5. The cable portion may surround and protect the wires from the surrounding environment. As shown, the wires terminate at a contact ring 444 along the device body. The sensor may transmit signals to the device body through the wires and the contact ring. The device body may process and transmit data signals that represent measurements obtained by the sensor. The device body may include an integrated circuit unit 415. Although not shown, the integrated circuit unit of the device body may have a processing unit, power source, internal clock, additional sensors, and/or a transmitter, such as those described above. In some embodiments, the integrated circuit component may be an RFID unit or a low power Wi-Fi device.

Figure 10:
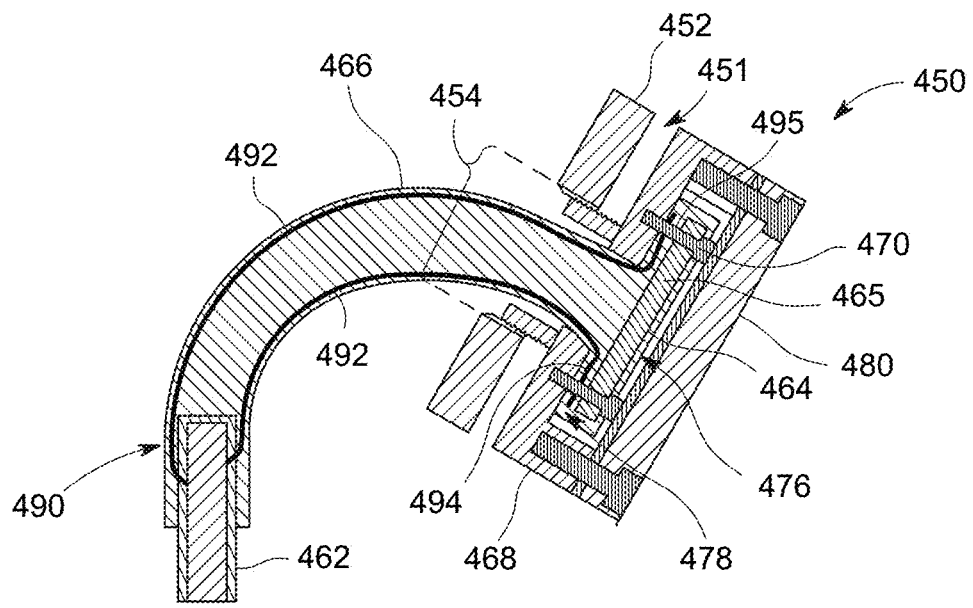
FIG. 10 is a cross-section of a portion of a wireless device utilizing the sensor of FIG. 4 in accordance with an embodiment.

FIG. 10 is a cross-section of a portion of a wireless device 450, which is coupled to a wall 452 of a tank 451. The wireless device may include similar features as the wireless device described with reference to FIG. 9. For example, the wireless device may include a sensor 462, a device body 464, and an intermediate cable portion 466 that joins the sensor and the device body. The wireless device may include a coupling component 468 that secures directly to the device body and the cable portion through one or more fasteners 470. In the illustrated embodiment, the coupling component is rotatably engaged to the wall in a similar manner as other coupling components.

To assemble the wireless device, the coupling component may be rotatably engaged to the wall. The sensor and the cable portion may be inserted through the coupling component and a fill port of the wall. The device body may be encased within a mating end 476 of the cable portion. As shown, the coupling component has a mating face 478 that faces in a direction away from the wall. Accordingly, the cable portion and the device body may be secured to the coupling component using the fasteners. A cover body 480 may be positioned over the cable portion to hold the device body between the cover body and the coupling component. The cable portion may not include a fill channel that permits access to the reservoir.

A trailing end 490 of the sensor is shown in FIG. 10. The trailing end is coupled to wires 492 that communicatively couple the sensor to the device body. As shown, the wires terminate at contacts 494, 495 that are coupled to the device body. The device body may include an integrated circuit component, which, in the illustrated embodiment, is a RFID unit. The sensor may transmit signals to the integrated circuit component through the wires.

FIG. 11 is a cross-section of a portion of a wireless device 500. The wireless device may be similar in some respects as other the wireless devices described herein. However, as shown in FIG. 11, the wireless device utilizes a sensor and a coupling component that can attach to a wall of a tank, which is a gear case in this illustrated embodiment. The wireless device includes a device body 530 that is operably coupled to the sensor through a base support 510 and an intermediate beam 512. The base support is disposed within an opening 514 of the coupling component. The beam extends between and joins the sensor and the base support. The beam may be fabricated from, for example, stainless steel and may provide a passageway 516 for wires 518 that communicatively couple the device body and a sensor 502.

The base support includes a mating face 520 that faces away from the tank 508. The mating face has contacts 524, 525 thereon. The contact may be a contact pad, and the other contact may be a ring contact that extends around the contact pad. The device body may be rotatably engaged to a coupling component 504. The device body includes a mounting surface 532 that faces the mating face and has corresponding contacts that are configured to engage the contacts. More specifically, when the device body is rotated to engage the coupling component, the mounting surface of the device body may advance toward the mating face so that the contacts of the device body press against and engage the contacts.

Accordingly, the device body may be communicatively coupled to the sensor. Similar to the device bodies described above, the device body may include an integrated circuit component 515 having a processing unit and a transmitter (not shown). Optionally, the integrated circuit component may include a memory, an internal clock, and one or more other sensors. The integrated circuit component may transform the signals from the sensor (or memory or other sensors) into data signals. The data signals may then be transmitted to a reader (not shown). In some embodiments, the integrated circuit component is formed as an RFID unit.

FIG. 12 is a cross-section and FIG. 13 is a front view, respectively, of a portion of a wireless device 550. The wireless device may include a sensor (not shown) and a device body 552 that are communicatively coupled through wires 554. The device body is secured to a faceplate 556 that is coupled to an exterior surface of a tank 560 (FIG. 13). FIGS. 12 and 13 illustrate an embodiment in which no electrical contacts are required along the device body 552 to electrically join the sensor. Instead, wires (FIG. 12) from the sensor may extend through potting 562 that mechanically couples the sensor to the tank 560. Like the wireless device 400 (FIG. 9), the wireless device may permit access to a fill port 566 through a plug 568. Although not shown, the device body may include an integrated circuit component, such as those described above, that processes data signals and transmits data signals. The integrated circuit component may be an RFID unit that is directly coupled to one of the wires.

Figure 14:
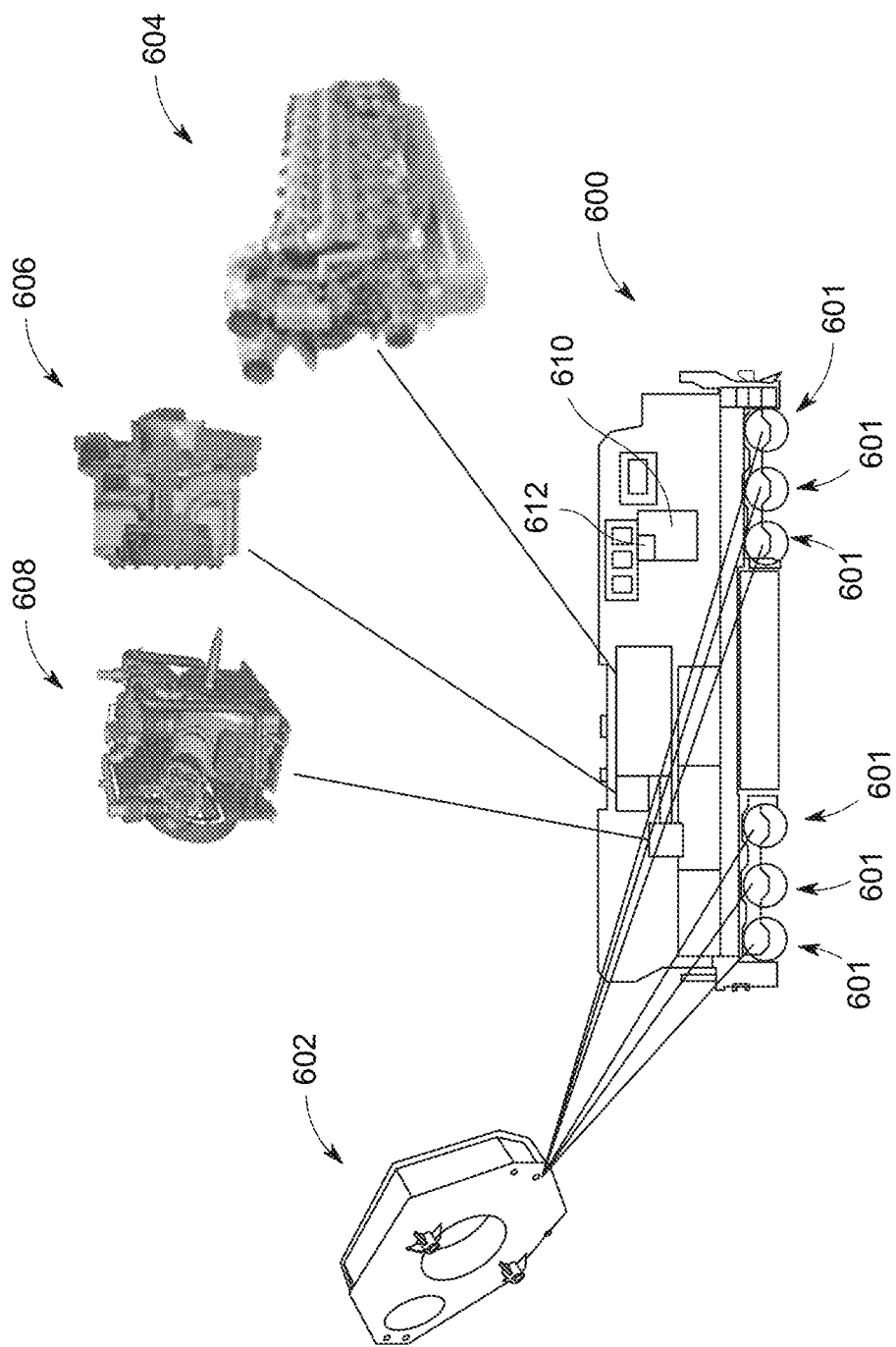
FIG. 14 is a schematic view of a locomotive and illustrates a plurality of components of the locomotive in accordance with an embodiment.

FIG. 14 is a schematic view of a rail vehicle, in this embodiment the rail vehicle is a locomotive 600, and illustrates a plurality of components of the locomotive that may include one or more wireless devices, such as the wireless devices described herein. For example, the locomotive may include a plurality of drive trains 601 that each has a gear case 602. The locomotive may include an engine 604, a turbo-charger 606 operably coupled to the engine, and an air compressor 608. Each of the components may have one or more of the wireless devices described herein operably coupled thereto. For example, the gear cases and the engine may have at least one of the wireless devices described above. In particular, each of the gear cases and the engine may have a reservoir that includes a liquid lubricant. The turbo-charger and the air compressor may use, for example, an accelerometer.

As shown, the locomotive may include an on-board control system 610. The control system can control the tractive efforts and/or braking efforts of the locomotive and, optionally, other locomotives that are directly or indirectly coupled to the locomotive. Operations of the control system may be based on inputs received from an operator of the locomotive and/or remote inputs from, for example, a control tower, a dispatch facility, or the like. In addition, the control system may receive inputs from various components of the locomotive. In some cases, the inputs may be data signals received through wireless communication. For example, the wireless devices of the gear cases, the engine, the turbo-charger, and the air compressor may wirelessly communicate data signals to the control system. The control system may include a reader 612 for receiving the wireless data signals. The control system may include a signal-processing module and a planning module that are similar to the signal-processing and planning modules described in FIG. 1. The planning module may generate operating plans for the locomotive based on the inputs received.

Figure 15:
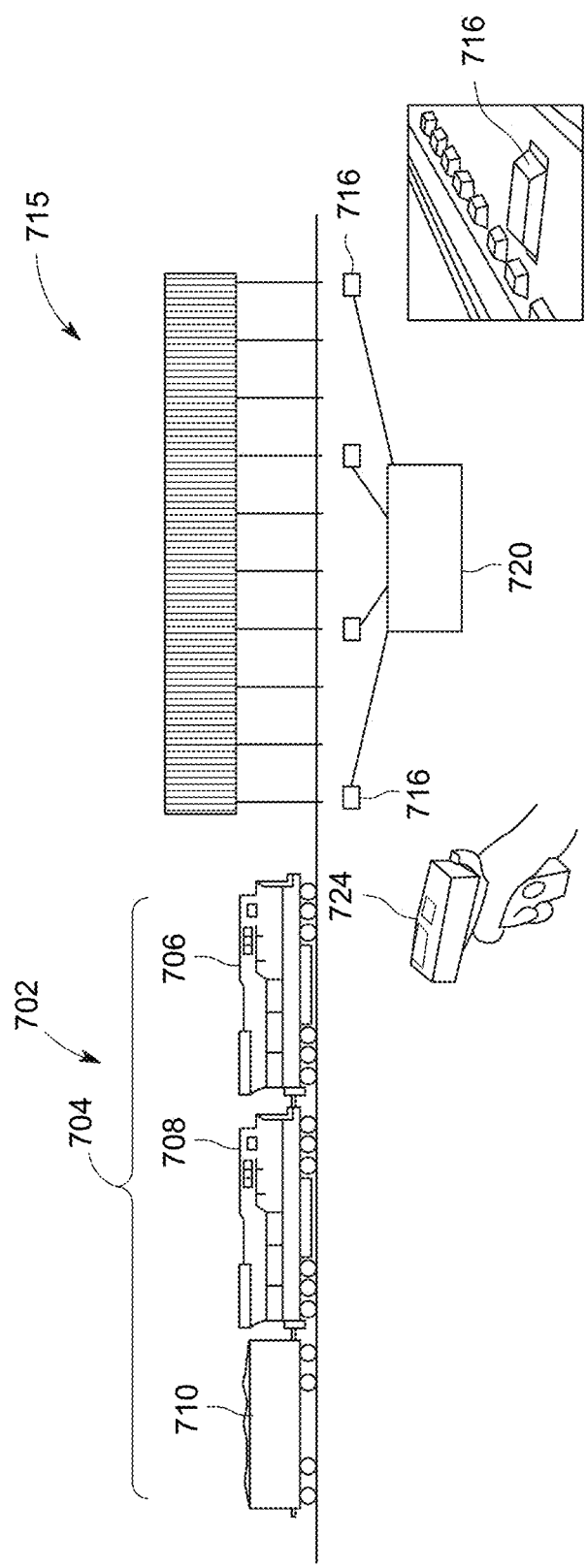
FIG. 15 illustrates a system in accordance with an embodiment for obtaining data signals from one or more wireless devices.
Figure 16:
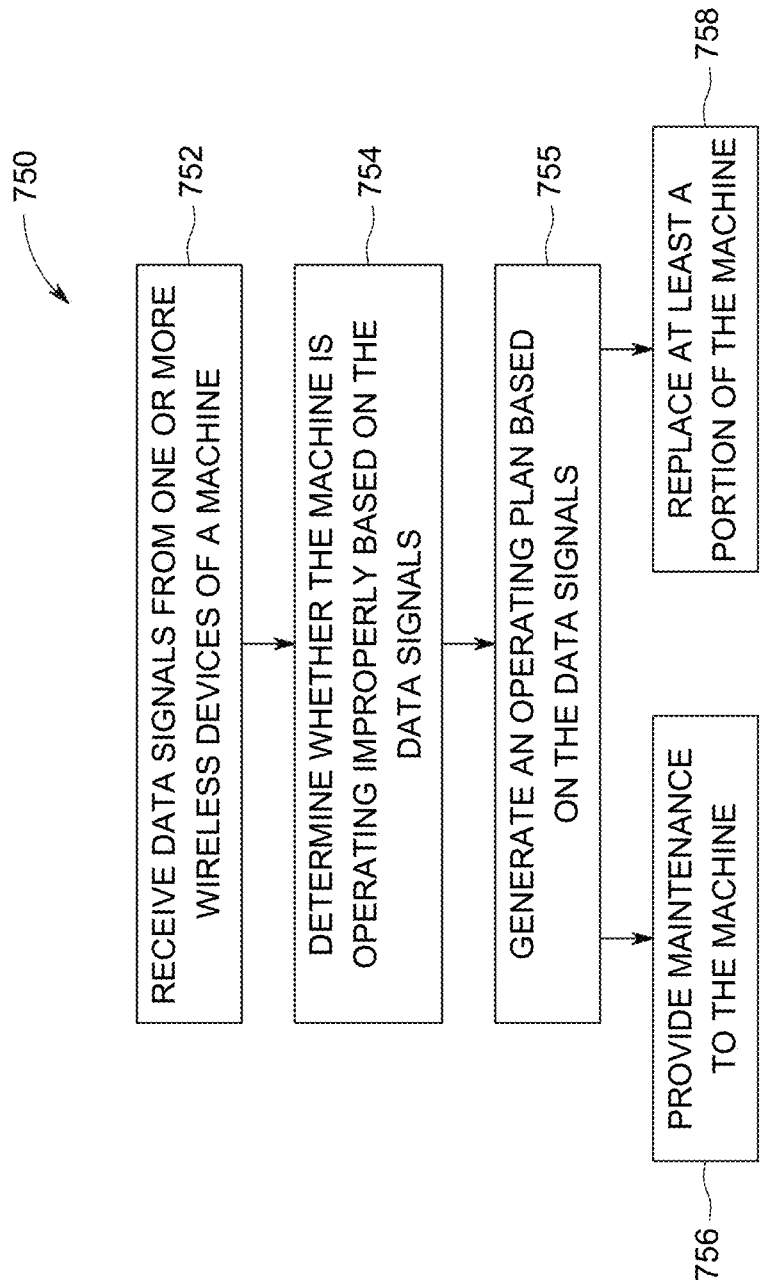
FIG. 16 is a flowchart illustrating a method in accordance with an embodiment.

FIG. 15 illustrates a system 700 in accordance with one embodiment for obtaining data signals from one or more wireless devices. FIG. 16 illustrates a flowchart of a method 750 that may be executed or performed by the inventive system. In some embodiments, a locomotive may execute or perform the method. The system and the method may employ structures or aspects of various embodiments discussed herein. In some embodiments, certain steps of the method may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. Likewise, the system is not required to include each and every feature of each and every embodiment described herein.

With respect to FIG. 15, the system includes a vehicle system 702 (e.g., train) including a locomotive consist 704. The locomotive consist may include at least one locomotive that is linked (physically or logically) to one or more rail vehicles. For example, FIG. 15 shows the locomotive consist including first and second locomotives 706, 708 and a rail car 710. In other embodiments, the vehicle system may include more rail cars. Each of the locomotives may include a plurality of components that are each monitored by one or more wireless devices. For example, each of the locomotives may include an engine, a turbo-charger, an air compressor, and a plurality of gear cases, such as those described herein.

As shown in FIG. 15, the vehicle system is approaching a designated reading location 715. The reading location is a maintenance facility in the illustrated embodiment. However, the reading location may be a variety of other locations that are capable of receiving wireless data signals from the locomotives. For example, the reading location may be a depot, fuel station, wayside location, rail yard entry point or exit point, designated sections of the track(s), and the like. The reading location includes a plurality of readers 716. Each of the readers is communicatively coupled (e.g., wirelessly or through communication wires) to a control system 720. Alternatively or additionally, a handheld reader 724 may be carried by an individual and used to receive the data signals. The reader may communicate data signals with the control system.

The control system may include a signal-processing module and a planning module, such as the signal-processing and planning modules described in FIG. 1. For example, the control system may generate operating plans that include instructions for operating the vehicle system and other similar vehicle systems.

The method may include receiving (at 752) data signals from one or more of the wireless devices of a machine. In the illustrated embodiment, the machine is the vehicle system or one of the locomotives. However, embodiments described herein are not necessarily limited to locomotives. The machine may have one or components with moving mechanical elements or parts. For example, the machine may have a drive train, engine, air compressor, and/or turbo-charger. The data signals may be representative of a measurement of an operative condition of the component. By way of example the measurement may be at least one of a vibration measurement, a capacitance of a liquid, a temperature of a liquid, a fluid conduction of a liquid, a dielectric constant of a liquid, an impedance of a liquid, or a viscosity of a liquid. In particular embodiments, the measurement is representative of a vibratory state of a gear case or of a liquid condition of a lubricant held in the gear case.

The receiving operation (at 752) may include receiving the data signals at one or more fixed readers having stationary positions. For example, the readers may have fixed positions with respect to tracks 730. The readers may be located at designated distance from the tracks so that the readers are capable of receiving the data signals. The receiving operation (at 752) may include receiving the data signals through one or more movable readers, such as the handheld reader. In an alternative embodiment, as described above, the receiving operation may occur with an on-board control system.

The method may include determining (at 754), based on the data signals, whether the component of the machine is operating improperly. For example, the control system may analyze the data signals and, optionally, other inputs to determine whether the component is operating sufficiently. If the component is operating improperly, the method may include generating (at 755) an operating plan and/or a shopping or maintenance plan that is based on the data signals. The operating plan may be a new (or revised) operating plan that can replace a currently-implemented operating plan. The method may include at least one of providing maintenance (at 756) to the component or replacing (at 758) an element of the component.

In an embodiment, a system (e.g., a monitoring system) is provided that includes a sensor that can be disposed within a reservoir of a machine having moving parts that are lubricated by a liquid in the reservoir. The can measure liquid to determine a quantity or quality of the liquid in the reservoir. The system may include a device body operably coupled to the sensor. The device body has a processing unit coupled to the sensor that can generate first data signals that are representative of the measurement of the liquid. The device body includes a transmitter that can wirelessly communicate the first data signals to a remote reader.

Figure 17:
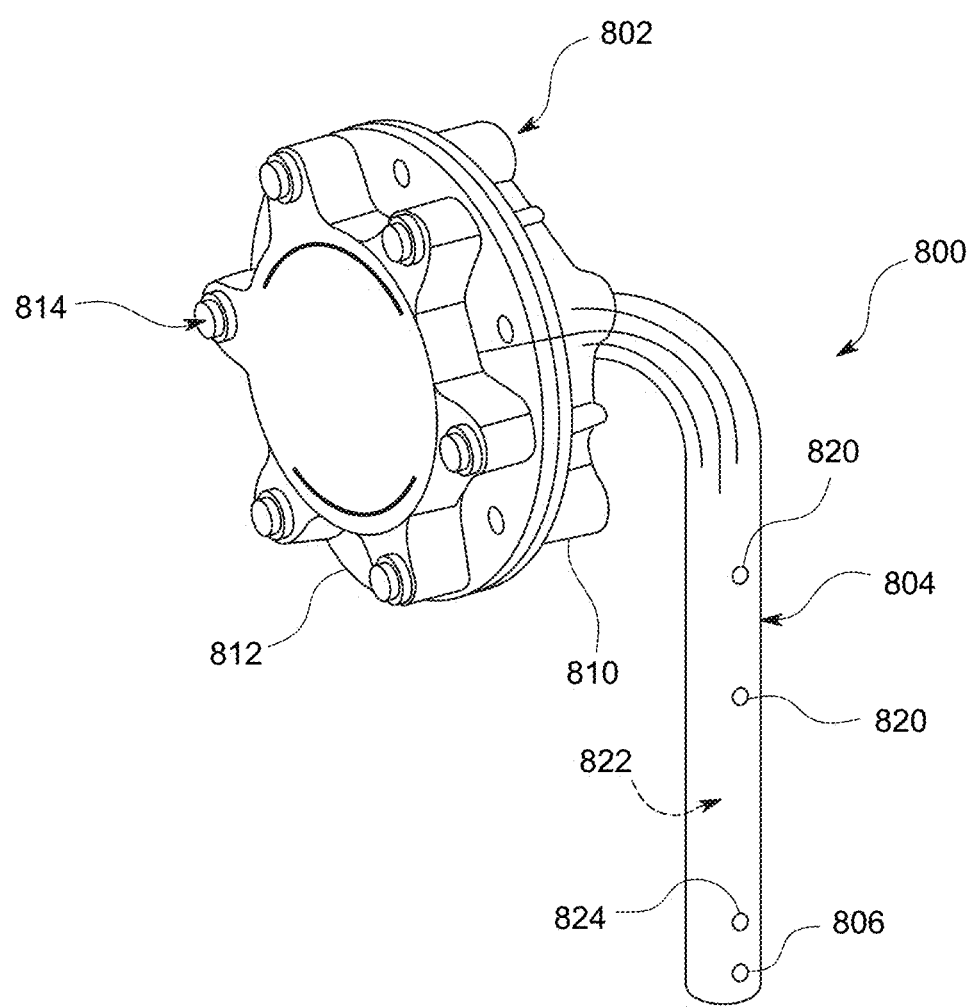
FIG. 17 is a perspective view of a wireless device in accordance with an embodiment.

With reference to FIG. 17, a sensor device 800 is shown that includes a housing 802 and a dipstick portion 804. The dipstick portion has a distal tip 806 spaced from the housing. The housing includes a base portion 810 and a cap portion 812. A series of fasteners 814 secure the cap portion to the base portion.

The dipstick portion has a plurality of apertures 820 disposed along the length of the dipstick portion. These apertures function as vent holes to relieve pressure as oil flows into an interior chamber 822 of the dipstick portion (described in more detail with reference to FIG. 18). The apertures 820 are referred to as vent apertures herein. In the illustrated embodiment, at least some of the vent apertures are defined on opposite sides of the dipstick portion. The vent apertures on opposite sides may be axially offset relative to each other along a length of the dipstick portion to structurally strengthen the dipstick portion by reducing weakness or failure points. The vent apertures may be the same size, as shown, or may have different sizes relative to each other. The number, size and placement of the vent apertures may be determined at least in part on application-specific parameters. The dipstick portion also defines at least one fluid entry aperture 824 that is located proximate to the distal tip. Each fluid entry aperture is configured to provide an access opening that allows fluid into the interior chamber of the dipstick portion.

The housing is configured to be coupled to a tank or reservoir that contains a fluid. When oriented in an upright manner during operation, the dipstick portion rests with the distal end near or in a volume of fluid to be tested. In one embodiment, fluid that contacts the dipstick portion may flow into the interior chamber through the at least one fluid entry aperture. The pressure in the dipstick portion is relieved by a corresponding loss of gas through the vent apertures. The release of gas allows the fluid within the interior chamber to rise to a level that corresponds to a fluid level of the fluid within the tank or reservoir.

Figure 18:
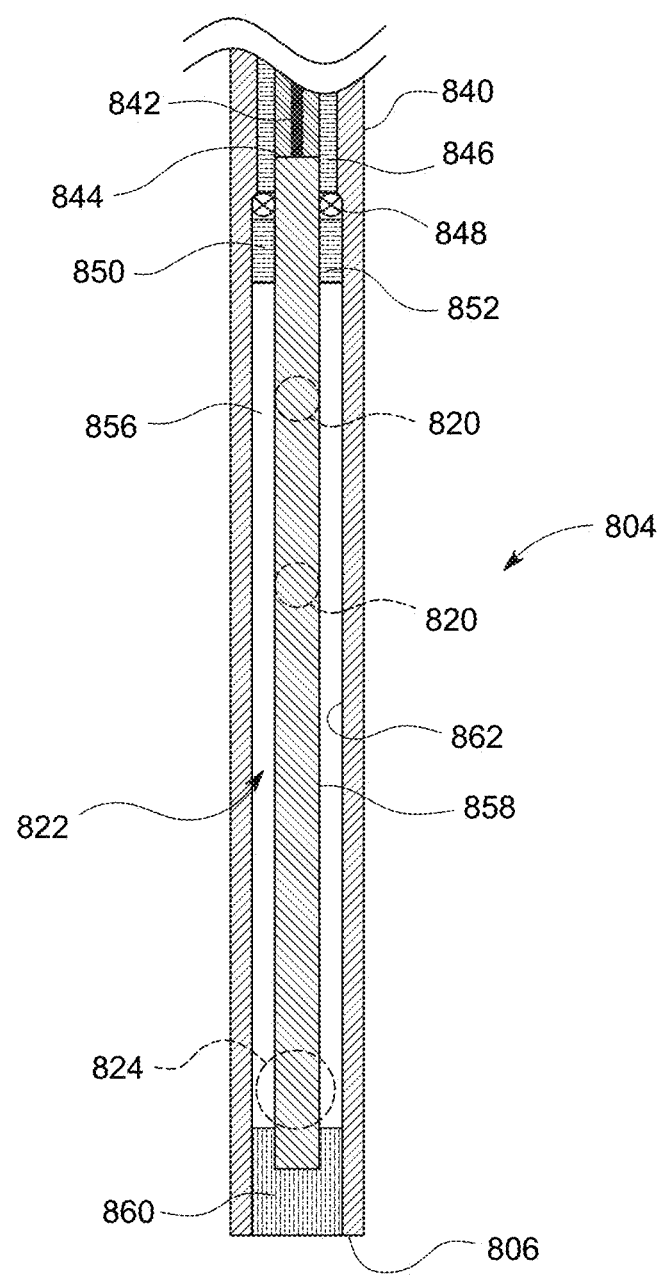
FIG. 18 is a schematic, cross-sectional side view of a portion of the wireless device shown in FIG. 17.

With reference to FIG. 18, the dipstick portion of the sensor device is shown as a cross-sectional cutaway with superimposed circles 820, 824 indicating where vent and fluid entry apertures, respectively, may be disposed. The dipstick portion may include a cylindrical outer tube 840 that houses a concentrically disposed wire 842 in an insulated sleeve 844. The sleeved wire is surrounded by a chemically resistant and electrically isolated inner tube 846 (e.g., a non-conductive tube). The inner tube may be formed of one or more plastics or other polymers, such as polytetrafluoroethylene (PTFE) or the like. At least one o-ring washer 848 may be placed around an electrode 850. A spacer member 852 provides sealing and support for the o-ring around the electrode. Another spacer 860 is disposed at the distal tip to secure and support a distal end of the electrode and to seal the bottom end of the tube. Thus, fluid that enters the interior chamber flows through a fluid entry aperture.

Suitable materials for use as the spacer members may include one or more plastics or other polymers, such as PTFE and/or polyetheretherketone (PEEK). A volume or void 856 is defined radially between an outer surface 858 of the electrode and an inner surface 862 of the outer tube 840. Fluid that enters the interior chamber of the dipstick portion flows through the volume. Silicone elastomers, such as SYLGARD (commercially available from Dow Corning) may be used as needed.

The cap portion and the base portion may be formed of metal. While not shown, brazing the joints between the cap portion and the base portion creates a stronger joining of the metal components than welding. Fasteners rather than tack welds have been used, too, in high impact environments to prohibit the housing from being damaged. The electronics package may be potted, or set, within the housing to reduce the effect of impact forces and shocks on the components inside the housing.

A stray capacitance control structure may be employed on the sensor device. In one embodiment, a G11 plate may be added to reduce or eliminate stray capacitance. The plate may be disposed between the housing and the dipstick portion. For example, the plate may be secured to the base portion of the housing. Alternatively, the stray capacitance control structure may be curved to extend at least partially around a perimeter of the housing to at least partially surround the electronic package held in the housing. In another alternative embodiment, the electronic package may be secured within the cap portion of the housing, and the stray capacitance control structure is a plate that extends across and is held at an interface defined between the cap portion and the base portion of the housing. Suitable materials for the stray capacitance control structure may include multi-layer ceramic capacitors or other materials with suitable permissivity values. Due to the stray capacitance control structure, the capacitance of the electronic package may be isolated from the sensor capacitance. Alternatively, the capacitance of the electronic package may be compensated for instead of being isolated or reduced relative to the sensor capacitance.

In the illustrated embodiment, the electrode is a continuous sensor that is elongate and extends at least a majority of the length of the dipstick portion. The continuous sensor may operate to provide a signal through the sleeved wire. An electrical characteristic (e.g., magnitude, signal strength, amplitude, etc.) of the electrical signal may be proportional to the amount of surface area of the electrode that contacts the fluid. That is, when the fluid level is high, a greater proportion of the electrode is in contact with the fluid than when the fluid level is low, and the resulting signal through the wire may be stronger. Alternatively, the sensor may include a series of discrete electrodes mounted on a support instead of, or in addition to, the elongate electrode. The electrodes may be spaced apart along an axial length of the dipstick portion. In such an arrangement, each electrode may be configured to signal when a fluid level is high enough to contact the respective electrode. Thus, one could judge a fluid level by noting which of the electrodes are transmitting a signal indicating contact with a fluid. Optionally, multiple wires may be used to transmit electrical signals from the multiple electrodes, or a multiplexer may be used to transmit the information along a single wire. The electrical characteristic of the electrical signal from the sensor may change based on the number of electrodes that contact the fluid. For example, the signal strength may increase at generally discrete levels or amounts with an increasing number of electrodes signaling contact with the fluid.

In another embodiment, in addition to the presence and quantity of fluid in the volume in the tube, the sensor may be used to measure other parameters of the fluid. These other parameters may include one or more of temperature, pressure, conductivity, resistance, viscosity, and turbidity of the fluid. Still other parameters may include the presence or absence of certain contaminants or constituents, such as carbon, water, oil or petroleum products and/or by-products, sulfur, metals, minerals, and biological materials. The presence of contaminants or constituents may be used to determine the health and/or age of the fluid. For example, the petroleum products and/or by-products may indicate degradation of the fluid used to determine the age of oil, gasoline, or another petroleum-based fluid. The concentration of water may indicate the health of the petroleum-based fluid. For instances where the fluid is a gas, the measured parameters may include the content of oxygen, nitrogen oxide, sulfur compounds, organo-phosphates, cyanates, and/or the like.

With additional reference back to FIG. 17, the wire communicates with an electronics package (not shown) disposed within a cavity inside of the cap and base portions of the housing. The electronics package may include, for example, one or more of the wireless devices disclosed herein for transmission of the electrical signals generated by the one or more sensors. In various embodiments, the electronics package also includes an accelerometer, a clock, an electro-magnetic sensor (such as a Hall Effect sensor), and/or an RFID sensor. These devices may be used to wake the sensor device from a "sleep" or "off" mode for the sensor device to collect data and/or transmit the collected data. The clock may allow the sensor device to collect data and/or transmit the collected data at a selectively determined time interval. The time interval may be based on a frequency of need or on a desired battery life/power use rate.

In a fleet setting, for example, the wireless device of the electronics package may wake and transmit an electrical signal at times that are offset from times that other wireless devices of the vehicle or machine, on which the sensor device is coupled, transmit respective electrical signals, or at different frequencies than the other wireless devices. This system of staggering communications may alleviate frequency bandwidth constraints, and may reduce the chance of interference between multiple devices. In one embodiment, the wireless device first checks if there is another wireless device transmitting at a specified frequency or range of frequencies before transmitting data.

Alternatively, or in addition, the wireless device may transmit in response to a trigger or stimulus. Suitable triggers may be based on the type of devices present on the electronics package. For example, if an accelerometer is disposed on the electronics package, a shock (e.g., an impact force) on the sensor device that exceeds a designated threshold may be the trigger. The trigger may be initiated by a tap on the wireless device. Furthermore, the trigger may be based on movement of the sensing device, such as rotating or shaking the sensor device. If the sensor device is coupled to a vehicle, then when the vehicle moves or stops, or if the vehicle goes over a bump, the collection/transmitting process may be triggered. If an electro-magnetic sensor is present, a magnetic or an electric field may be employed as desired to trigger the wireless device to collect and/or transmit sensor information. Similarly, if an RFID sensor is present, passing an RF transmitter may wake the sensor device.

In one aspect, the transmitter may be energized by the reader when the reader interrogates the transmitter. In one aspect, the system includes a power source that can supply power to the transmitter for transmitting the data signals. The power source may include, for example, a battery and/or energy harvesting device. The sensor may be at least partially submerged in the liquid. The measurement is at least one of a capacitance of the liquid, a temperature of the liquid, a fluid conduction of the liquid, a dielectric constant of the liquid, an impedance of the liquid, or a viscosity of the liquid. The device body may be affixed to a wall of the machine in which the wall at least partially defines the reservoir. The sensor and the device body collectively form a first wireless device. The system may include a second wireless device that can obtain and wirelessly communicate second data signals that are representative of a measurement of a different reservoir.

In one aspect, the sensor may be disposed in a gear case of a locomotive, the gear case having the reservoir. The transmitter is included in a radio-frequency identification (RFID) element. The sensor, the processing unit, and the transmitter collectively form a first wireless device. The system may include a second wireless device that can obtain and wirelessly transmit data signals that are representative of a measurement of a different reservoir. The system may include a signal-processing module. The signal-processing module may determine, based on the data signals, whether the machine is operating improperly by comparing the data signals of the first wireless device to the data signals of the second wireless device.

In an embodiment, the fluid is gear box lubricant and the sensor/electrode measures the amount of lubricant present. During operation, the wireless device of the sensor device may transmit to a vehicle controller and/or to an off-board service center the lubricant level value. In response to receiving a sensor reading indicating a low lubricant condition in a gearbox being monitored by the sensor device, the vehicle controller may respond by removing a supply of power and/or torque to the axle for the associated gearbox. In a multi-axle system, the vehicle may continue along a trip or mission using other powered axles. This isolation of axles associated with gearboxes having low lubricants may be advantageous in a locomotive that may be in a consist with other locomotives. Other activities may be initiated in response to detecting a low lubricant condition, such as requesting or scheduling maintenance for the vehicle (e.g., entering a shopping order where maintenance or repair services are scheduled). Furthermore, the vehicle may be directed to detour from a prior mission to travel to a repair and maintenance shop for adding lubricant or otherwise addressing the low lubricant issue.

In one aspect, the data signals are configured to be transmitted to a handheld reader. In another aspect, the data signals are configured to be transmitted to a fixed reader located along a railway track. In yet another aspect, the data signals are configured to be transmitted to an on-board reader located on a locomotive. The sensor includes a multi-conductor capacitive sensor configured to detect a capacitance of a fluid. The fluid may function as a dielectric, wherein a level of the fluid affects the capacitance detected. In another aspect, the sensor includes a body float and a position transducer configured to detect a position of the body float. The position transducer may include, for example, a reed switch.

In an embodiment, a system (e.g., a monitoring system) is provided that includes a sensor that may be engaged to a mechanical element of a drive train to obtain a measurement of a vibratory state of the mechanical element. The measurement is representative of an operative condition of the drive train. The system includes a device body that has a processing unit operably coupled to the sensor. The processing unit is configured to generate first data signals representative of the measurement. The device body also includes a transmitter that can wirelessly communicate the first data signals to a remote reader.

In one aspect, the system includes a power source configured to supply power to the transmitter for transmitting the data signals. The system includes a memory. The memory is configured to log a plurality of the measurements obtained at different times. The transmitter is configured to transmit data signals that include the measurements. The sensor, the processing unit, and the transmitter collectively form a first wireless device. The system may include a second wireless device configured to obtain and wirelessly transmit data signals that are based on a measurement of a different drive train. The device body includes a radio-frequency identification (RFID) unit. The RFID unit may have the processing unit and the transmitter.

In an embodiment, a method (e.g., a method for monitoring an operative condition of a machine) includes receiving data signals from a wireless device of a machine having a drive train. The wireless device includes a device body directly coupled to the drive train. The device body includes a transmitter for wirelessly transmitting the data signals. The data signals may be based on a measurement of an operative condition of the drive train. The method also includes, responsive to determining that the drive train is operating improperly, generating signals to schedule at least one of maintenance of the drive train or replacement of an element of the drive train. The measurement is representative of vibratory state of a gear case or a liquid condition of a lubricant held in the gear case. The measurement is at least one of a vibration measurement of a gear case, a capacitance of a lubricant stored by the gear case, a temperature of the lubricant, a fluid conduction of the lubricant, a dielectric constant of the lubricant, impedance of the lubricant, or a viscosity of the lubricant.

In one aspect, the data signals are received from a plurality of wireless devices. The data signals are based on a common type of measurement. The data signals are received at a handheld reader. The machine is a locomotive and the data signals are received at a fixed reader located along a railway track. The machine is a locomotive and the data signals are received at a reader located on-board the locomotive. The method also includes operating the machine according to a first operating plan and generating a second operating plan that is based on the operative condition.

In an embodiment, a system (e.g., a monitoring system) includes a signal-processing module that can receive data signals from a wireless device of a machine having a drive train. The data signals are based on a measurement of an operative condition of the drive train. The signal-processing module is configured to determine, based on the data signals, whether the drive train is operating improperly. Optionally, the system also includes a planning module that can generate an operating plan that is based on the operative condition. A system (e.g., wireless liquid monitoring system) comprises a sensor, a processing unit, and a transmitter. The sensor may be disposed within a reservoir of a machine having moving parts that are lubricated by a liquid in the reservoir. The sensor is configured to obtain a measurement of the liquid that is representative of at least one of a quantity or quality of the liquid in the reservoir. The processing unit is operably coupled to the sensor and configured to generate first data signals representative of the measurement of the liquid. The transmitter is operably coupled to the processing unit and configured to wirelessly communicate the first data signals to a remote reader.

In another embodiment of the system, alternatively or additionally, the system may be disposed in the machine (and when installed is actually disposed in the machine), which comprises a vehicle or other powered system comprising the reservoir, the moving parts, and one or more computers or other controller-based units (e.g., a vehicle controller) other than the processing unit. The system may not be physically electrically connected (e.g., not connected by wires or other conductors) to any of the one or more computers or other controller-based units in the machine. Thus, the first data signals may only wirelessly transmitted from the system to the reader or elsewhere, and are not transmitted via wire/cables or other physical electrical connections.

In another embodiment of the system, alternatively or additionally, the processing unit and transmitter are co-located proximate to one another (e.g., at least partially integrated onto a common circuit board, positioned within a common box/housing that is positioned within the machine—that is, the common box/housing is not coextensive with the outer body/structure of the machine, but is located within the outer body/structure—and/or some or all of the components of the processing unit and transmitter are located within 10 cm of each other, within 5 cm of each other, etc., for example), and/or at least portions of the processing unit and transmitter are directly connected to a wall of the reservoir (e.g., a wall that bears a pressure of and/or contacts the liquid in the reservoir) and/or to a structure immediately connected to such a wall (e.g., support structure of the reservoir, gear case, or the like).

In one embodiment, the fluid is lubricating oil for a vehicle that, during operation, is at a temperature that is greater than 100 degrees Celsius. The sensor is configured to withstand extended immersion in the fluid and repeated shocks or forces greater than 100 G (e.g., 100 times the force of gravity) during operation of the vehicle without significant degradation in the sensor's measurement capabilities.

In another embodiment of the system, alternatively or additionally, the transmitter can wirelessly communicate the first data signals to the remote reader that comprises: a remote reader located within the machine (e.g., if the machine is a vehicle, the remote reader is located with the vehicle); a remote reader located on a wayside of a route of the machine, the machine comprising a vehicle; a portable (handheld, or otherwise able to be carried by a human operator) remote reader.

In one embodiment, a system includes a sensor, one or more processors, a transmitter, and a capacitance control structure. The sensor is configured to contact a fluid and measure a characteristic of the fluid. The one or more processors are operably coupled to the sensor. The one or more processors are configured to generate one or more data signals representative of the characteristic of the fluid that is measured by the sensor. The transmitter is operably coupled to the one or more processors. The transmitter is configured to wirelessly communicate the one or more data signals to a remote reader. The capacitance control structure is configured to one or more of reduce or isolate sensor capacitance of the sensor from the one or more processors.

In an aspect, the sensor is configured to measure at least the capacitance of the fluid. The fluid functions as a dielectric. The one or more processors are configured to detect a level of the fluid based at least in part on the capacitance that is measured.

In an aspect, the sensor comprises a multi-conductor capacitive sensor configured to measure at least the capacitance, inductance, and resistance of the fluid. The sensor is configured to detect one or more qualities of the fluid based on at least one of the capacitance, inductance, and resistance that is measured.

In an aspect, the one or more processors and the transmitter are disposed in a housing and the sensor is disposed in a tube that is secured to the housing. The housing is configured to be coupled to a tank or reservoir that contains the fluid. The tube is configured to contact the fluid within the tank or reservoir when the housing is coupled to the tank or reservoir.

In an aspect, the tube is elongate and defines a plurality of axially disposed apertures. The tube is configured to receive the fluid within an interior chamber of the tube through at least one of the apertures to contact an electrode of the sensor that is disposed within the interior chamber.

In an aspect, at least two of the apertures are axially offset relative to each other.

In an aspect, the system further includes at least one of an accelerometer, an electro-magnetic sensor, a radio-frequency identification device, or a clock that is operably coupled to the one or more processors.

In an aspect, the system further includes a clock operably coupled to the one or more processors. The clock cooperates with the one or more processors to wake the system from an inactive state to an active state at a determined time or time interval to measure the fluid and transmit the one or more data signals based on the sensed measurement of the fluid.

In an aspect, the system is one of a plurality of like systems. The one or more processors and the clock are configured to wake the system and control the system to transmit the one or more data signals at times that are different from the waking and transmission times of other systems of the plurality of like systems.

In an aspect, the system further includes an accelerometer operably coupled to the one or more processors. The accelerometer cooperates with the one or more processors to wake the system from an inactive state to an active state in response to detecting an impact force on the system that exceeds a determined threshold impact value. The system in the active state measures the fluid and transmits the one or more data signals based on the sensed measurement of the fluid.

In an aspect, the system further includes an accelerometer operably coupled to the one or more processors. The accelerometer is configured to wake the system from an inactive state to an active state after a period of inactivity in response to detecting at least one of a lack of motion or a vibration of the system. The system in the active state measures the fluid and transmits the one or more data signals based on the sensed measurement of the fluid.

In an aspect, the sensor is operable to measure at least one of a fluid level of the fluid, a temperature of the fluid, a fluid conductivity, a dielectric constant of the fluid, an impedance of the fluid, or a viscosity of the fluid.

In an aspect, the system further includes a device body that includes a memory. The memory is configured to store a plurality of the measurements obtained by the sensor at different times. The one or more data signals communicated by the transmitter include at least one of the measurements.

In an aspect, the fluid is lubricating oil for a vehicle. The sensor is configured to withstand extended immersion in the fluid at a temperature that is greater than 100 degrees Celsius and to withstand repeated shocks that are greater than 100 G during operation of the vehicle without significant degradation in an operational quality or accuracy of the sensor.

In an aspect, the system further includes a vehicle controller communicatively coupled to the one or more processors. The vehicle controller is configured to detect a fluid level of a fluid associated with a first powered axle of a vehicle having a plurality of powered axles; respond to a detected fluid level being below a determined threshold value by one or more of reducing or eliminating power to the first powered axle; and operate the vehicle using other powered axles as the first powered axle is operated with one or more of reduced or no power.

In an aspect, the fluid comprises one or more of lubricant, fuel, coolant, or exhaust gas.

In one embodiment, a method includes detecting a fluid level of lubricant in a first gearcase reservoir in a vehicle. The method also includes responding to a detected fluid level being below a determined threshold value by one or more of reducing or eliminating power supplied to a first powered axle of the vehicle that is associated with the first gearcase reservoir. The method further includes operating the vehicle using at least a second powered axle that is coupled to a second gearcase reservoir while the first powered axle is supplied one or more of reduced or no power.

In an aspect, the method further includes signaling to a repair or maintenance shop that the vehicle is in need of service or maintenance.

In one embodiment, a method includes generating, from time to time, one or more data signals from a first wireless device of a sensor device. The first wireless device is housed in a device body of the sensor device that is configured to be coupled to a machine. The sensor device further includes a sensor configured to contact a fluid associated with the operation of the machine. The machine is one of a fleet of machines with each machine in the fleet having at least one respective wireless device. The method also includes determining when to generate the one or more data signals from the first wireless device such that the first wireless device generates the one or more data signals at a different time or in a different time period than other wireless devices of the machines in the fleet.

In an aspect, the first wireless device has a clock. The one or more data signals generated from the first wireless device are determined based on a predetermined time indicated by the clock that differs from other times associated with other wireless devices of the machines in the fleet.

As used herein, an element or step recited in the singular and proceeded with the word "a" or "an" should be understood as not excluding plural of said elements or steps, unless such exclusion is explicitly stated. Furthermore, references to "one embodiment" of the presently described inventive subject matter are not intended to be interpreted as excluding the existence of additional embodiments that also incorporate the recited features. Moreover, unless explicitly stated to the contrary, embodiments "comprising," "including," or "having" (or like terms) an element, which has a particular property or a plurality of elements with a particular property, may include additional such elements that do not have the particular property.

As used herein, terms such as "system," "module," "processor" or "controller" may include hardware and/or software that operate(s) to perform one or more functions. For example, a system, module, or controller may include a computer processor or other logic-based device that performs operations based on instructions stored on a tangible and non-transitory computer readable storage medium, such as a computer memory. Alternatively, a system, module, or controller may include a hard-wired device that performs operations based on hard-wired logic of the device. The systems, modules, and controllers shown in the Figures may represent the hardware that operates based on software or hardwired instructions, the software that directs hardware to perform the operations, or a combination thereof.

As used herein, terms such as "operably connected," "operatively connected," "operably coupled," "operatively coupled" and the like indicate that two or more components are connected in a manner that enables or allows at least one of the components to carry out a designated function. For example, when two or more components are operably connected, one or more connections (electrical and/or wireless connections) may exist that allow the components to communicate with each other, that allow one component to control another component, that allow each component to control the other component, and/or that enable at least one of the components to operate in a designated manner.

It is to be understood that the subject matter described herein is not limited in its application to the details of construction and the arrangement of elements set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on pre-AIA 35 U.S.C. § 112, sixth paragraph, or post-AIA § 112(f), unless and until such claim limitations expressly use the phrase "means for" followed by a statement of function void of further structure.

This written description uses examples to disclose several embodiments of the inventive subject matter, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A method, comprising:
   coupling a housing of a detection assembly to a first gearcase reservoir of a vehicle, the housing containing an electronics package positioned within the housing, the detection assembly including a tube secured to the housing and containing a sensor positioned within the tube, wherein the tube is elongate and defines a plurality of axially disposed apertures;
   coupling a capacitance control structure to the housing, the capacitance control structure configured to one or more of reduce or isolate a sensor capacitance of the sensor from the electronics package;
   detecting, by the sensor, a fluid level of lubricant in the first gearcase reservoir;
   responding to the detected fluid level being below a threshold value by one or more of reducing or eliminating power supplied to a first powered axle of the vehicle that is associated with the first gearcase reservoir; and
   operating the vehicle using at least a second powered axle that is coupled to a second gearcase reservoir while the first powered axle is supplied one or more of reduced or no power.

2. The method of claim 1, further comprising signaling to a repair or maintenance shop that the vehicle is in need of service or maintenance.

3. The method of claim 1, wherein coupling the capacitance control structure to the housing comprises coupling a capacitance control plate to the housing, the capacitance control plate curved to at least partially surround the electronics package.

4. The method of claim 1, wherein the housing includes a cap portion and a base portion, the tube secured to the housing at the base portion and the electronics package contained within the cap portion, wherein coupling the capacitance control structure to the housing comprises coupling the capacitance control structure to the housing between the cap portion and the base portion.

5. A system, comprising:
   a detection assembly comprising:
     a housing configured to be coupled to a first gearcase reservoir of a vehicle;
     a tube secured to the housing, wherein the tube is elongate and defines a plurality of axially disposed apertures;
     a sensor positioned within the tube and configured to contact a fluid associated with a first powered axle of the vehicle and measure a fluid level of the fluid in the first gearcase reservoir;
     an electronics package positioned within the housing, the electronics package comprising:
       one or more processors operably coupled to the sensor, the one or more processors configured to generate one or more data signals representative of the fluid level of the fluid that is measured by the sensor; and
       a transmitter operably coupled to the one or more processors, the transmitter configured to wirelessly communicate the one or more data signals to a remote reader; and a capacitance control structure coupled to the housing and configured to one or more of reduce or isolate a sensor capacitance of the sensor from the electronics package; and a vehicle controller communicatively coupled to the remote reader and configured to:

respond to the measured fluid level being below a designated threshold value by one or more of reducing or eliminating power to the first powered axle; and operate the vehicle using a second powered axle of the vehicle as the first powered axle is operated with one or more of reduced or no power.

6. The system of claim 5, wherein the sensor is configured to measure at least the capacitance of the fluid, the fluid functioning as a dielectric, the one or more processors configured to detect a level of the fluid based at least in part on the measured capacitance.

7. The system of claim 5, wherein the sensor comprises a multi-conductor capacitive sensor configured to measure at least the capacitance, inductance, and resistance of the fluid, the sensor configured to detect one or more qualities of the fluid based on at least one of the measured capacitance, inductance, and resistance.

8. The system of claim 5, wherein the tube is configured to contact the fluid within the first gearcase reservoir when the housing is coupled to the first gearcase reservoir.

9. The system of claim 5, wherein the tube is configured to receive the fluid within an interior chamber of the tube through at least one of the apertures to contact an electrode of the sensor that is disposed within the interior chamber.

10. The system of claim 9, wherein at least two of the apertures are axially offset relative to each other.

11. The system of claim 5, further comprising at least one of an accelerometer, an electro-magnetic sensor, a radio-frequency identification device, or a clock that is operably coupled to the one or more processors.

12. The system of claim 5, further comprising a clock operably coupled to the one or more processors, the clock cooperating with the one or more processors to wake the system from an inactive state to an active state at a determined time or time interval to measure the fluid and transmit the one or more data signals based on the sensed measurement of the fluid.

13. The system of claim 12, wherein the system is one of a plurality of like systems, the one or more processors and the clock being configured to wake the system and control the system to transmit the one or more data signals at times that are different from the waking and transmission times of other systems of the plurality of like systems.

14. The system of claim 5, further comprising an accelerometer operably coupled to the one or more processors, the accelerometer cooperating with the one or more processors to wake the system from an inactive state to an active state in response to detecting an impact force on the system that exceeds a determined threshold impact value, the system in the active state measuring the fluid and transmitting the one or more data signals based on the sensed measurement of the fluid.

15. The system of claim 5, further comprising an accelerometer operably coupled to the one or more processors, the accelerometer configured to wake the system from an inactive state to an active state after a period of inactivity in response to detecting at least one of a lack of motion or a vibration of the system, the system in the active state measuring the fluid and transmitting the one or more data signals based on the sensed measurement of the fluid.

16. The system of claim 5, wherein the sensor is operable to measure at least one of a fluid level of the fluid, a temperature of the fluid, a fluid conductivity, a dielectric constant of the fluid, an impedance of the fluid, or a viscosity of the fluid.

17. The system of claim 5, wherein the fluid is lubricating oil for a vehicle, the sensor being configured to withstand extended immersion in the fluid at a temperature that is greater than 100 degrees Celsius and to withstand repeated shocks that are greater than 100 G during operation of the vehicle without significant degradation in an operational quality or accuracy of the sensor.

18. The system of claim 5, wherein the fluid comprises one or more of lubricant, fuel, coolant, or exhaust gas.

19. The system of claim 5, wherein the capacitance control structure includes a capacitance control plate, the capacitance control plate curved to at least partially surround the electronics package.

20. The system of claim 5, wherein the housing includes a cap portion and a base portion, the tube secured to the housing at the base portion and the electronics package contained within the cap portion, wherein the capacitance control structure is coupled to the housing between the cap portion and the base portion.

* * * * *